(12) United States Patent
Davis et al.

(10) Patent No.: US 7,261,701 B2
(45) Date of Patent: Aug. 28, 2007

(54) SKIN ANTISEPTIC COMPOSITION DISPENSER AND METHODS OF USE

(75) Inventors: Robert A. Davis, Cottage Grove, MN (US); Matthew T. Scholz, Woodbury, MN (US); Mark V. Johnson, Afton, MN (US); Triet M. Lu, Woodbury, MN (US); Robert A. Asmus, Hudson, WI (US); John D. Dell, St. Paul, MN (US)

(73) Assignee: 3M Innovative Properties Co., St. Paul, MN (US)

( * ) Notice: Subject to any disclaimer, the term of this patent is extended or adjusted under 35 U.S.C. 154(b) by 574 days.

(21) Appl. No.: 10/263,518

(22) Filed: Oct. 3, 2002

(65) Prior Publication Data

US 2004/0068218 A1 Apr. 8, 2004

(51) Int. Cl.
 A61M 35/00 (2006.01)
 B43K 5/14 (2006.01)
 A46B 11/04 (2006.01)
(52) U.S. Cl. .................. 604/3; 604/289; 604/306; 604/310; 401/135; 401/276
(58) Field of Classification Search ............... 604/1–3, 604/289, 306, 310, 411, 415; 401/132–135, 401/207, 266, 138, 196, 270, 272, 276, 277; 132/320; 15/104.93, 104.94, 244.1, 244.2, 15/244.3, 244.4; 222/80, 81, 541.1–541.9
See application file for complete search history.

(56) References Cited

U.S. PATENT DOCUMENTS

| D4,390 S | 10/1870 | Atwater |
| 188,227 A | 3/1877 | Bacon |
| 2,481,803 A | 9/1949 | Weaver ........................ 120/36 |
| D171,592 S | 3/1954 | Gore ............................... D9/2 |
| 3,059,262 A | 10/1962 | Marschner ..................... 15/244 |
| 3,137,880 A | 6/1964 | Kubit et al. ................... 15/244 |
| 3,215,263 A | 11/1965 | Mathison ..................... 206/47 |
| 3,490,001 A * | 1/1970 | Meyers et al. ............... 340/2.2 |

(Continued)

FOREIGN PATENT DOCUMENTS

EP 0 232 596 A1 * 8/1987

(Continued)

OTHER PUBLICATIONS

ThomasNet, Foam: Hydrophilic Polyurethane, http://www.thomasnet.com/products/foam-hydrophilic-polyurethane-30682314-1.html.*

(Continued)

*Primary Examiner*—Karin Reichle
*Assistant Examiner*—Michael G Bogart
(74) *Attorney, Agent, or Firm*—Nancy M. Lambert

(57) ABSTRACT

Skin antiseptic composition dispensers and methods of use are disclosed. The skin antiseptic composition dispenser may include a container with one or more walls that are substantially impermeable to ethylene oxide gas during normal ethylene oxide sterilization processes. In some embodiments, the container may include flexible walls free of metallic foil barrier layers. The containers may also include one or more vents in addition to one or more openings used to dispense the skin antiseptic composition within the container. The dispenser may include an applicator with a hydrophilic foam.

18 Claims, 4 Drawing Sheets

U.S. PATENT DOCUMENTS

| | | | | |
|---|---|---|---|---|
| 3,792,699 | A | | 2/1974 | Tobin et al. .................... 128/2 |
| 3,804,592 | A | * | 4/1974 | Garbe ........................ 422/124 |
| D245,221 | S | | 8/1977 | Hoyt ........................... D7/178 |
| 4,050,826 | A | | 9/1977 | Berghahn et al. ........... 401/196 |
| 4,155,139 | A | | 5/1979 | Corcoran ..................... 15/244 |
| 4,304,869 | A | | 12/1981 | Dyke ........................ 435/296 |
| D268,447 | S | | 3/1983 | Sudduth ..................... D32/45 |
| 4,393,106 | A | * | 7/1983 | Maruhashi et al. ........ 428/36.7 |
| 4,507,111 | A | | 3/1985 | Gordon et al. ................. 604/3 |
| 4,542,012 | A | | 9/1985 | Dell ............................ 424/28 |
| 4,584,192 | A | | 4/1986 | Dell et al. .................... 424/81 |
| 4,747,719 | A | | 5/1988 | Parkin ........................ 401/132 |
| 4,799,815 | A | | 1/1989 | Barabino et al. ........... 401/132 |
| 4,856,136 | A | | 8/1989 | Janssen ..................... 15/244.3 |
| 4,925,327 | A | | 5/1990 | Wirt ........................... 401/205 |
| 4,934,011 | A | | 6/1990 | Haug .......................... 15/145 |
| 4,939,184 | A | * | 7/1990 | Kennedy .................... 521/170 |
| 5,027,803 | A | | 7/1991 | Scholz et al. ................. 128/89 |
| 5,084,931 | A | | 2/1992 | Kuhlcke .................... 15/244.1 |
| 5,100,028 | A | | 3/1992 | Seifert ........................ 222/107 |
| 5,133,971 | A | | 7/1992 | Copelan et al. ............. 424/448 |
| 5,288,159 | A | | 2/1994 | Wirt ........................... 401/133 |
| 5,308,180 | A | | 5/1994 | Pournoor et al. ........... 401/205 |
| 5,323,589 | A | | 6/1994 | Linner ......................... 53/432 |
| 5,326,603 | A | | 7/1994 | Van Dyke et al. ............ 428/35 |
| 5,341,538 | A | | 8/1994 | Banome .................... 15/210.1 |
| D351,229 | S | | 10/1994 | Wirt ........................... D24/119 |
| 5,435,660 | A | | 7/1995 | Wirt ........................... 401/135 |
| 5,473,860 | A | | 12/1995 | Linner ......................... 53/432 |
| 5,489,022 | A | | 2/1996 | Baker ......................... 206/439 |
| 5,490,736 | A | | 2/1996 | Haber et al. .................. 401/40 |
| 5,577,907 | A | | 11/1996 | Linner ........................ 432/159 |
| 5,592,713 | A | | 1/1997 | Rones ....................... 15/210.1 |
| D377,978 | S | | 2/1997 | Haber et al. ............... D24/119 |
| 5,658,084 | A | | 8/1997 | Wirt ........................... 401/132 |
| D383,631 | S | | 9/1997 | Wirt et al. ................... D6/545 |
| D384,184 | S | | 9/1997 | Dewey ......................... D28/7 |
| D384,457 | S | | 9/1997 | Morissette ................... D32/51 |
| D386,640 | S | | 11/1997 | Wirt et al. ................... D6/545 |
| 5,769,552 | A | | 6/1998 | Kelley et al. ................ 401/132 |
| 5,791,801 | A | * | 8/1998 | Miller ........................ 401/132 |
| 5,799,841 | A | | 9/1998 | Wirt ............................ 222/571 |
| D406,426 | S | | 3/1999 | Henrie ......................... D32/51 |
| 5,897,031 | A | | 4/1999 | Wirt et al. .................. 222/179 |
| 5,908,350 | A | | 6/1999 | Walters ....................... 451/524 |
| 5,915,746 | A | | 6/1999 | Melcher et al. ............... 29/450 |
| 6,050,271 | A | * | 4/2000 | Spencer ...................... 132/112 |
| 6,293,431 | B1 | * | 9/2001 | Seymour et al. .............. 222/83 |
| 6,299,377 | B1 | * | 10/2001 | Emerit et al. ................ 401/266 |
| 6,410,599 | B1 | | 6/2002 | Johnson ...................... 514/634 |
| 6,422,778 | B2 | * | 7/2002 | Baumann et al. ........... 401/266 |
| 6,474,508 | B1 | | 11/2002 | Marsh ......................... 222/83 |
| 6,488,665 | B1 | | 12/2002 | Severin et al. .............. 604/200 |
| 6,505,985 | B1 | | 1/2003 | Hidle et al. .................. 401/134 |
| 6,533,484 | B1 | | 3/2003 | Osei et al. ................... 401/205 |
| 6,585,693 | B1 | | 7/2003 | Dischler ..................... 604/171 |
| 6,672,784 | B2 | * | 1/2004 | Baumann et al. ........... 401/266 |
| 6,910,822 | B2 | * | 6/2005 | Hidle et al. ................. 401/134 |
| 6,918,710 | B2 | | 7/2005 | Budds et al. ............... 401/132 |
| 6,976,494 | B2 | * | 12/2005 | Wayne et al. ............... 132/108 |
| 2001/0055511 | A1 | | 12/2001 | Baumann et al. |
| 2002/0076258 | A1 | | 6/2002 | Crosby et al. .............. 401/205 |
| 2004/0267182 | A1 | | 12/2004 | Davis et al. ................... 604/2 |
| 2006/0072962 | A1 | | 4/2006 | Cybulski et al. ............ 401/205 |

FOREIGN PATENT DOCUMENTS

| | | |
|---|---|---|
| ES | 200001073 | 11/2000 |
| WO | WO94/13352 A1 * | 6/1994 |
| WO | 051578 | 6/1999 |

OTHER PUBLICATIONS

Conney; "Skin Care Antiseptics"; May-Aug. 2002, p. 402, item "E", "PrepStick Plus". Retrived from internet using Google advanced catalog search Sep. 15, 2005, <URLwww.conney.com> (2 pgs.).

Decisions for the Mold Designer, p. 71.

Standards & Practices of Plastics Molders—1998 Edition, p. 30.

Sponge applicator since 2000, 2 pages of photocopies of the sponge applicator.

* cited by examiner

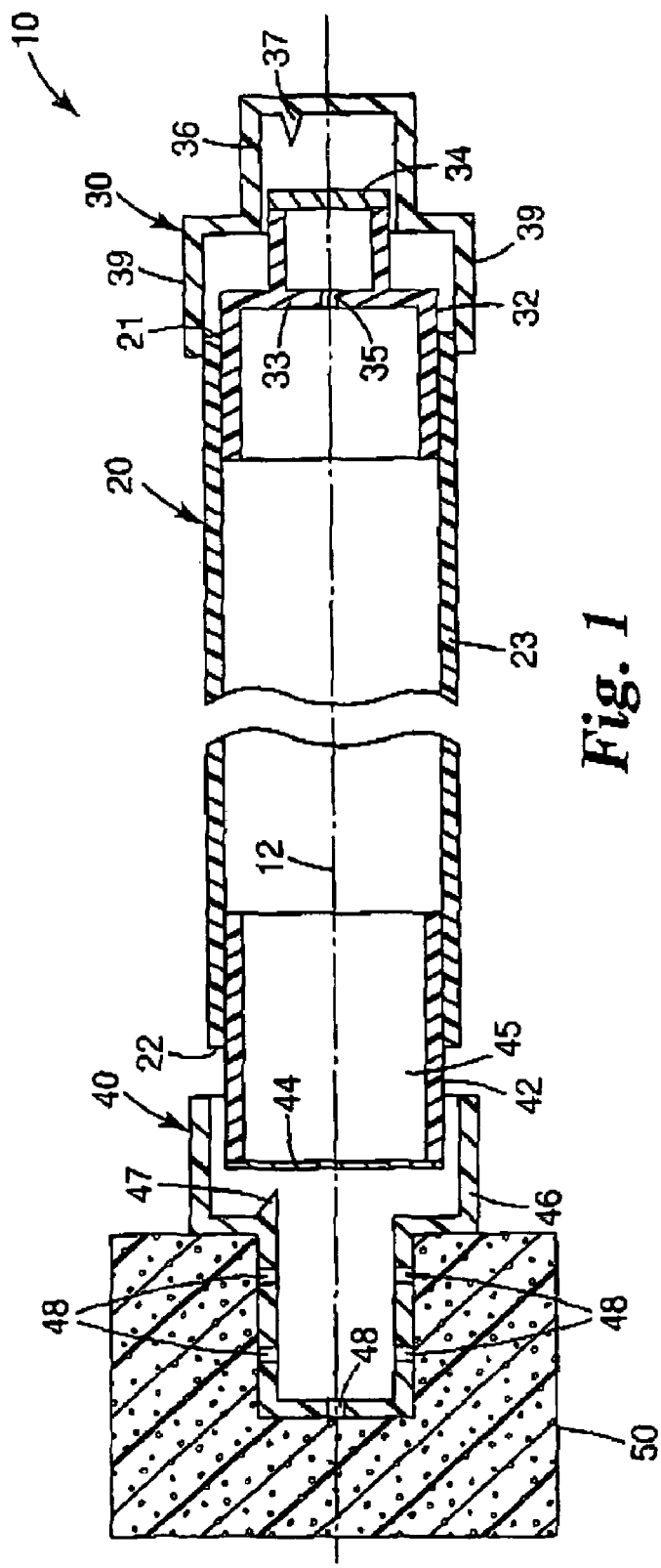
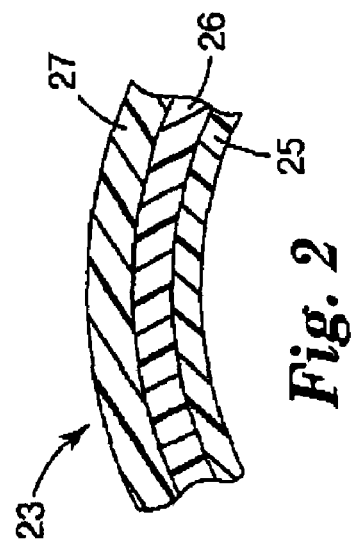
Fig. 1
Fig. 2

SKIN ANTISEPTIC COMPOSITION DISPENSER AND METHODS OF USE

FIELD OF THE INVENTION

The present invention relates to the field of skin antiseptic composition dispensers.

BACKGROUND

Antiseptic preparation of patient's skin for surgery conventionally includes a 3-10 minute scrubbing of the affected area with an antiseptic soap solution followed by the application of a water-soluble antiseptic paint solution.

These solutions are generally applied with saturated sponges that are attached to a blade or held with forceps. These sponges are often saturated by soaking them in open pans of solution. Sometimes, sponges with attached handles are provided in a plastic or aluminum foil laminate pouch containing enough liquid to saturate the sponges. In some products the sponges are supplied dry in a sterile "kit" with the antiseptic solutions provided in relatively thin walled 4 oz. polyethylene bottles. These bottles generally have wall thickness less than about 500 microns.

While inexpensive, these techniques are messy and offer little control over inadvertent dripping of the solution into areas where it is undesired. Since many of the available solutions contain active ingredients such as alcohol and iodine which can be irritating if allowed to pool in areas and left in contact with the skin, good control over the application has long been desirable.

Over the years, devices have been developed in an attempt to prevent solution dripping associated with these techniques, and to reduce the time required for application of the antiseptic solution. In particular, the DURAPREP products commercially available from 3M Company (St. Paul, Minn.) have enjoyed commercial success by providing substantially drip-free, convenient application of antiseptic solutions.

Coassigned U.S. Pat. No. 4,925,327 describes a liquid applicator that incorporates a rigid, porous metering insert to regulate the flow rate of liquid between the applicator handle and a foam sponge covering a major orifice of the handle. The liquid to be dispensed is contained in a rupturable reservoir removably affixed at the other major orifice of the handle.

Coassigned U.S. Pat. No. 5,658,084 further discloses a liquid applicator where the liquid is contained in a frangible ampoule inside the body of the applicator. This ampoule is supported and protected by a deformable element that prevents unintentional breakage of the ampoule from impact during storage and handling before use. The applicator is actuated by pushing at least a portion of the frangible ampoule through an aperture in the deformable element and into contact with a means for breaking the ampoule.

One consideration in the design of these delivery devices is to prevent contact between the clinician and the skin of the patient to avoid contamination. This may be accomplished by providing a handle that is preferably at least four inches long and oriented at an angle of 30-90 degrees to the head of the sponge. While this is convenient for application to skin, it is completely unsuitable for applying an antiseptic solution into, e.g., the vaginal canal. In contrast, typical sponge sticks available in kits have the sponge and handle in the same plane. While this is suitable for prepping the vaginal canal, it is difficult to use on skin because of a high potential for contact between the clinician's hand and the patient.

U.S. Pat. No. 4,507,111 illustrates still another surgical scrub dispensing system. In this invention the antiseptic prep solution is housed in a separate elongated cartridge adapted to be longitudinally slidable in an elongated hollow handle member. The handle member has attached thereto an absorbent sponge. The handle member further includes two hollow spikes formed on the inside of said member which provide flow communication from the interior of the hollow handle member to the absorbent sponge. When the spikes puncture the elongated handle one of the spikes serves to vent the container and one of the spikes serves to deliver the fluid. Since both spikes reside on one end of the container they must be spaced and the handle held at a precise angle to ensure a fluid head difference necessary for proper venting. Many clinicians have been trained to hold the applicators in a vertical orientation when activating. This applicator would not, however, properly vent when held vertically.

Typical antiseptic composition applicators are provided with sterile exterior surfaces to avoid contaminating the patient with microorganisms that could be located on the exterior surfaces of the applicators. Many of these applicators are sterilized by exposure to ethylene oxide gas. Surprisingly, we have found that kits containing iodophor-based antiseptic compositions in polyethylene bottles having wall thicknesses of less than about 500 microns contain significant levels of iodohydrin (2-iodoethanol). Iodohydrin is considered quite toxic and is believed to be formed by reaction of ethylene oxide which has penetrated through the container with hydrogen iodide found in the antiseptic composition. Ethylene oxide itself is also quite toxic and its by product levels in medical devices are tightly controlled by the Food and Drug Administration. Similar problems may result from sterilization by others gases such as hydrogen peroxide plasma and the like. Therefore, even in non-iodophor containing antiseptic compositions, it is highly desirable to prevent ethylene oxide and other chemical sterilants from diffusing into the container during sterilization.

U.S. Pat. No. 4,799,815 describes a liquid dispensing swab applicator system in which a hermetically sealed fluid filled tube having an absorbent swab at one end is opened by puncturing the tube with an external jig. The fluid flows out over the exterior surface of the tube and into the swab. This delivery method may not, however, be practical for larger fluid volumes of low viscosity fluids that need to be delivered rapidly (such as presurgical fluids) because the fluid exits at a rate much faster than the absorbent could absorb the fluid resulting in excessive dripping and mess.

While these products have provided a considerable advance, they are complex to manufacture, placing them beyond the means of some health care consumers.

SUMMARY OF THE INVENTION

The present invention provides skin antiseptic composition dispensers and methods of use that, in various embodiments, may provide a variety of advantages.

In some embodiments, the skin antiseptic composition dispenser may include a container with one or more walls that are substantially impermeable to ethylene oxide gas during normal ethylene oxide sterilization processes. Reactive sterilants such as ethylene oxide may react with the active antimicrobial agent or with other components in the skin antiseptic composition altering the potency or producing potentially toxic compounds. For example, iodine, as well as other antimicrobial agents, potentially react with ethylene oxide that passes into the container during sterilization of the exterior surfaces of the dispensers. The effectiveness of such skin antiseptic compositions may be compromised by exposure to ethylene oxide gas.

In some embodiments, it may be desirable to provide a container that includes flexible walls free of metallic foil barrier layers. A potential advantage of using containers free of metallic foil barrier layers is that if a metallic foil layer such as, e.g., aluminum foil, is exposed to a skin antiseptic composition containing iodine (e.g., an iodophor composition), the amount of iodine in the antiseptic composition may be rapidly reduced. Exposure of the antiseptic composition to metallic foil layers may be through, e.g., pinholes, or other defects in a coating that is otherwise meant to prevent direct contact between the antiseptic composition and the metallic foil layer. Reduction of the iodine levels in the antiseptic composition may be associated with a reduction in the antiseptic efficacy of the composition.

Another potential advantage of containers made with walls that are free of metallic foil barrier layers is that the walls may preferably be translucent or transparent. Walls that are translucent or transparent may allow for visual monitoring of the skin antiseptic composition within the container. In contrast, walls that include metallic foil barrier layers are typically opaque, thus preventing visual monitoring of the contents of the container.

A further potential advantage of containers made with walls that are free of metallic foil barrier layers is that the containers may be, in some instances, easily and inexpensively extruded. Extruded tubular containers can be produced free of, e.g., fin seals, that may be prone to leakage.

The skin antiseptic composition dispensers may also include one or more vents in addition to one or more openings used to dispense the skin antiseptic composition within the container. The vents may assist in dispensing of the skin antiseptic composition from the container to the applicator. The vents are preferably sealed and the skin antiseptic composition dispenser may include structures to assist in opening of the seal by twisting or other simple motions. In some instances, the vent seal may be opened by peeling.

In some embodiments, the skin antiseptic composition dispenser includes an applicator with a hydrophilic foam that may be helpful in reducing or preventing dripping of the skin antiseptic composition from the applicator during use. Surprisingly, hydrophilic foams have also been shown to provide superior antimicrobial efficacy as compared to conventional hydrophobic foam pads (when used with aqueous skin antiseptic compositions). The hydrophilic foam may, e.g., have an apparent surface energy of 35 dynes/centimeter or more. Even higher apparent surface energy may be desirable in connection with some skin antiseptic compositions, e.g., apparent surface energy of 40 dynes/centimeter or more may be preferred. It may, however, be preferred that the hydrophilic foams used as applicators in the present invention have an apparent surface energy of 45 dynes/centimeter or more, possibly 50 dynes/centimeter or more. In some instances, it may be preferred that the hydrophilic foam be wettable by deionized water (thus having, e.g., an apparent surface energy of 70 dynes/centimeter or more).

In some embodiments, the applicator may include a canted major surface that forms an angle with a longitudinal axis of the handle (e.g., the container) of the dispenser. The canted major surface may provide for clearance between the hand of the user and the patient's skin to reduce the likelihood of or prevent contact between the user's hand and the patient's skin during application of the skin antiseptic composition. If the angle formed by the canted major surface is not too large, the skin antiseptic dispenser may be used to apply skin antiseptic composition to the skin as well as within body orifices, e.g., vagina, rectum, etc.

In one aspect, the present invention provides a skin antiseptic composition dispenser including a container defining an interior volume; skin antiseptic composition located within the interior volume of the container; a spout attached to the container, wherein the spout has at least one opening therein; a dispensing seal located between the interior volume of the container and the spout; and a foam pad located over the spout, wherein the foam pad includes hydrophilic foam with an apparent surface energy of 35 dynes per centimeter or more.

In another aspect, the present invention comprises a skin antiseptic composition dispenser including a container defining an interior volume, wherein the container has a tubular shape that comprises one or more flexible walls free of metallic foil layers; skin antiseptic composition located within the interior volume of the container; and dispensing means for dispensing the skin antiseptic composition. The container is impermeable to liquid and vapor phases of the skin antiseptic composition and the container exhibits permeability to gaseous ethylene oxide of 20 mg/hr/cm$^2$ or less.

In another aspect, the present invention provides a skin antiseptic composition dispenser including a container defining an interior volume, wherein the container includes a tubular shape with one or more flexible walls free of metallic foil layers; skin antiseptic composition located within the interior volume of the container; and dispensing means for dispensing the skin antiseptic composition. The container is impermeable to liquid and vapor phases of the skin antiseptic composition; and the one or more flexible walls free of metallic foil layers include an inner layer and an outer layer, wherein at least one of the inner layer and the outer layer is substantially impermeable to ethylene oxide.

In another aspect, the present invention provides a skin antiseptic composition dispenser including a container defining an interior volume, wherein the container has a first end distal from a second end along a longitudinal axis; skin antiseptic composition located within the interior volume of the container; at least one dispensing opening proximate the first end of the container; a dispensing seal closing the at least one dispensing opening; at least one vent orifice proximate the second end of the container; a vent seal closing the at least one vent orifice; and an applicator attached to the first end of the container, wherein the at least one dispensing opening is in fluid communication with the applicator when the dispensing seal is opened. The skin antiseptic composition enters the applicator through the dispensing opening under the force of gravity when the dispensing seal and the vent seal are opened and the at least one vent orifice is located above the at least one dispensing opening.

In another aspect, the present invention provides a method of preparing a skin antiseptic composition dispenser for use by: providing a skin antiseptic composition dispenser as described in the preceding paragraph; opening the dispensing seal, wherein the at least one dispensing opening is in fluid communication with the applicator; opening the vent seal, wherein the vent orifice is open; and orienting the container such that the vent orifice is located above the dispensing opening, whereby the skin antiseptic composition flows into the applicator.

In another aspect, the present invention provides a method of preparing a skin antiseptic composition dispenser for use by: providing a skin antiseptic composition dispenser having a container defining an interior volume, skin antiseptic composition located within the interior volume of the container, an applicator attached to the container, and a liquid impermeable sleeve, wherein the applicator is located within the liquid impermeable sleeve; moving the skin antiseptic composition from the container into the applicator, wherein the skin antiseptic composition not retained by the applicator is retained within the liquid impermeable sleeve; and removing the applicator from the liquid impermeable sleeve after moving the skin antiseptic composition from the container into the applicator.

These and other features and advantages of the invention may be described more completely below in connection with various illustrative embodiments of the skin antiseptic dispensers and methods of using them.

BRIEF DESCRIPTION OF THE DRAWING

FIG. 1 is a cross-sectional view of one illustrative skin antiseptic composition dispenser according to the present invention.

FIG. 2 is a cross-sectional view of a portion of another skin antiseptic composition dispenser according to the present invention.

DETAILED DESCRIPTION OF ILLUSTRATIVE EMBODIMENTS OF THE INVENTION

Figure 3:
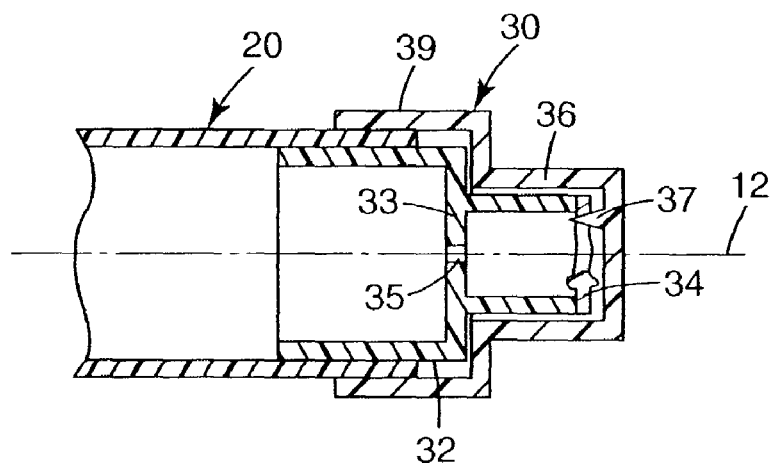
FIG. 3 is a cross-sectional view of one vent assembly for a skin antiseptic composition dispenser according to the present invention.

FIG. 1 is an illustrative embodiment of a skin antiseptic composition dispenser that includes many aspects of the skin antiseptic composition dispensers of the present invention. It should, however, be understood that all of the features depicted in the skin antiseptic composition dispenser of FIG. 1 need not necessarily be present in all skin antiseptic composition dispensers according to the present invention. In other words, the features of the skin antiseptic composition dispenser depicted in FIG. 1 may be used in concert or various combinations of the features may be employed to achieve some of the advantages possible in light of the present invention.

The skin antiseptic composition dispenser 10 of FIG. 1 includes a container 20 that in the illustrative embodiment is in the form of a tubular shape with a wall 23 extending between ends 21 and 22. The container 20 may be in the form of a tube having a circular cross-section, although tubular containers with other cross-sectional shapes may be used (e.g., oval, elliptical, hexagonal, rectangular, etc.). Tubes in the shape of right cylinders may, however, be desired for their stiffness, ease of manufacture, etc. Manufacturing the containers by extrusion may be useful to produce relatively thin (e.g., wall thickness of less than 1000 micrometers, possibly less than 750 micrometers, and possibly less than 500 micrometers) structures that may also function as barriers to sterilizing gases such as ethylene oxide.

The containers used in applicators of the present invention may be used as handles. When used as a handle, the container may typically have an aspect ratio (i.e., length: diameter) of at least 2, in some instances at least 4, and in other instances at least 6.

For use in preparation for a small surgical procedure, the amount of skin antiseptic composition in the containers used in connection with the present invention should generally be able to cover an area of, e.g., 10 square centimeters or more, and thus typically have volume of, e.g., 5-15 milliliters (ml). For larger surgical procedures, the applicator should be able to cover at least the torso of a large person, e.g., at least about 500-600 square centimeters. To cover that larger area, the container may typically have a volume of skin antiseptic composition of at least 20 ml, preferably at least 25 ml, and more preferably at least 30 ml.

The containers used in connection with the present invention may be filled with a skin antiseptic composition that includes (as the antimicrobial agent) iodine, an iodine complex, chlorhexidine, chlorhexidine salts, or combinations thereof. Preferred iodine complexes may include iodophors, e.g., povidone-iodine USP. Preferred chlorhexidine salts may include, e.g., chlorhexidine digluconate and chlorhexidine diacetate. Other suitable antimicrobial agents may include C2-C5 lower alkyl alcohols (including, e.g., ethyl alcohol, 1-propanol, and 2-propanol), parachlorometaxylenol (PCMX), triclosan, hexachlorophene, fatty acid monoesters of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants, and polymers that include a (C12-C22)hydrophobe and a quaternary ammonium group, polyquaternary amines such as polyhexamethylene biguanide, quaternary ammonium silanes, silver, silver salts (such as silver chloride), silver oxide and silver sulfadiazine, methyl, ethyl, propyl and butyl parabens, octenidene, peroxides (e.g., hydrogen peroxide and benzoyl peroxide), and the like, as well as combinations thereof.

Among the challenges associated with using such skin antiseptic compositions is the need to sterilize the exterior of the applicator while minimizing potential byproducts that may be produced when the composition is exposed to sterilization compounds such as ethylene oxide gas. Reactive sterilants such as ethylene oxide may react with the active antimicrobial agent or with other components in the skin antiseptic composition altering the potency or producing potentially toxic compounds. For example, typical high density polyethylene bottles having wall thicknesses of less than about 500 micrometers allow ethylene oxide through quite readily and result in iodophor preps having iodohydrin levels of 100 parts per million (ppm) or more, in some instances 200 ppm or more, and in some instances even as high as 600 ppm.

Another challenge is that the effectiveness of the skin antiseptic compositions may be compromised by exposure to ethylene oxide gas. For example, iodine as well as other antimicrobial agents may potentially react with ethylene oxide—which could alter the efficacy of the skin antiseptic composition.

To address these challenges, it may be advantageous to construct the container wall or walls of a material or materials that are functionally impermeable to ethylene oxide gas. The material or materials selected are also preferably capable of effectively storing a skin antiseptic composition that includes iodine, an iodine complex, chlorhexidine, chlorhexidine salts or combinations thereof, as well as other antimicrobial agents, for suitable time periods under typical storage conditions.

In addition to the above concerns, it may be desirable to provide a container that includes flexible walls free of metallic foil barrier layers. As used in connection with the invention, "flexible walls" means walls that can be compressed or otherwise deformed by hand to dispense the skin antiseptic composition located within the container without fracturing or leakage. As used in connection with the invention, "metallic foil barrier layers" means layers of metals or metallic compounds that typically function as barriers to the passage of constituents in the skin antiseptic composition, e.g., gases, liquids, vapors, etc. The phrase "free of metallic foil barrier layers" should not be construed to include layers that may include metallic particles located within, e.g., a polymeric binder, provided that the metallic particles do not form a continuous metallic foil layer that acts as a barrier layer.

Another potential advantage of using containers free of metallic foil barrier layers is that if a metallic foil layer such as, e.g., aluminum foil, is exposed to a skin antiseptic composition containing iodine (e.g., an iodophor composition), the amount of iodine in the antiseptic composition may be rapidly reduced. Exposure of the antiseptic composition to metallic foil layers may be through, e.g., pinholes, or other defects in a coating that is otherwise meant to prevent direct contact between the antiseptic composition and the metallic foil layer. Reduction of the iodine levels in the antiseptic composition may be associated with a reduction in the antiseptic efficacy of the composition.

Another potential advantage of containers made with walls that are free of metallic foil barrier layers is that the walls may preferably be translucent or transparent. Walls that are translucent or transparent may allow for visual monitoring of the skin antiseptic composition within the container. In contrast, walls that include metallic foil barrier layers are typically opaque, thus preventing visual monitoring of the contents of the container.

In some embodiments, it may be desirable to include ceramic barriers to enhance the barrier properties of the flexible walls free of metallic foil barrier layers. The flexible walls may, for example, include a ceramic layer with a thickness of, e.g., 200 micrometers or less, possibly 100 micrometers or less, and in some cases 50 micrometers or less. Thinner ceramic barrier layers may enhance flexibility of the walls. An example of such a ceramic barrier is marketed as CERAMIS (available from Alcan, Inc., Montreal, Canada). One potential advantage of containers with polymeric walls is that the containers may be manufactured by polymer extrusion and lamination techniques.

In embodiments of the invention that include containers with flexible walls free of metallic foil barrier layers, the walls of the containers are preferably impermeable to liquid and vapor phases of the skin antiseptic composition located within the containers. It will be understood that the impermeability is not complete, i.e., some small portion of one or more components within the skin antiseptic composition may pass through the walls of the containers, but the portions that pass under typical conditions will be functionally insignificant. For example, typical containers packaged as to be shipped (i.e., properly filled and sealed) placed in a convection oven at 60 degrees Celsius for 14 days will typically lose 2% or less by weight of the contents, and preferably 1% or less (with a sample size of at least five containers).

In addition to impermeability of the container walls, it is also preferred that, for those embodiments of containers used in connection with skin antiseptic compositions that are sensitive to ethylene oxide exposure (such as, e.g., iodine and other antimicrobial agents) the flexible walls exhibit a permeability to gaseous ethylene oxide of 20 mg/hr/cm$^2$ or less. In some embodiments, the permeability to gaseous ethylene oxide may be 10 mg/hr/cm$^2$ or less, possibly as low as 1 mg/hr/cm$^2$ or less. The permeability to gaseous ethylene oxide of polymeric walls in containers of the present invention is determined in accordance with the "Gaseous Ethylene Oxide Permeability" test described below.

One example of a polymer wall construction that may be suitable for containers used with iodine-containing skin antiseptic compositions is depicted in an enlarged cross-sectional view in FIG. 2. The depicted polymeric wall is a multilayer construction including an inner layer 25, an optional intermediate layer 26, and outer layer 27. Although the inner layer 25, intermediate layer 26, and outer layer 27 are each depicted as a single homogenous layer, it will be understood that each of those layers may include one or more sub-layers, particles, filaments, etc.

The inner layer 25 faces the interior volume of the container 20 and may preferably provide an impermeable barrier to liquid and vapor phases of one or more components of the skin antiseptic composition located within the container 20. In some embodiments, it may be preferred that the inner layer 25 also be capable of forming heat seal bonds either with itself (where, for example, the tube is compressed at one end to form a flat seal) or with other components inserted into, for example, an end of a cylindrical container. For example, the inner layer 25 may be a polyolefin (e.g., polyethylene such as high density polyethylene, etc.) that is a good barrier to water vapor and may also serve as a thermally scalable layer.

The outer layer 27 is located outside of the inner layer 25 relative to the interior volume of the container 20. The outer layer 27 may preferably provide the limited permeability to gaseous ethylene oxide as discussed above. Although the term outer layer is used herein, it should be understood that the outer layer 27 may or may not form the actual exterior surface of the container. In other words, additional layers may be provided as the exterior of the containers according to the present invention.

Gaseous ethylene oxide barrier layers may be the inner layer, outer layer, and/or the intermediate layer. In FIG. 2, the outer layer 27 is the barrier layer and may also be impermeable to one or more components of the skin antiseptic composition within the container 20. For example, a polyethylene terephthalate (PET) layer could be used to prevent alcohol (e.g., ethanol or 2-propanol) in a skin antiseptic composition from evaporating out of the container 20. When the antiseptic composition contains alcohol, it may be preferred that at least one layer of the container walls be manufactured of a material that is impermeable to alcohol in the antiseptic compositions (as the term "impermeable" is described above).

The intermediate layer 26 may be provided to function as a tie layer between the inner layer 25 and the outer layer 27 where the materials of the inner layer 25 and the outer layer 27 will not exhibit sufficient attachment to each other. The intermediate layer 26 may be an adhesive, extruded polymeric layer, etc.

In one example of a suitable multilayer polymeric wall construction for use in connection with the present invention, one of the inner layer 25 and the outer layer 27 may be formed of polyolefin, e.g., polyethylene (including, but not limited to, low density polyethylene, linear low density polyethylene, medium density polyethylene, high density polyethylene, metallocene polyethylenes, and mixtures thereof), polypropylene, ethylene/propylene copolymers, ethylene/butylenes copolymers, etc.

A second layer selected from the inner layer 25 and the outer layer 27 may be formed of, e.g., polyesters (e.g., polyethylene terephthalate and polybutylene terephalate), fluorinated layers such as polytetrafluoroethylene (PTFE, e.g., TEFLON), polyamides (e.g., nylon), chlorotriflouroethylene (ACLAR), polyvinylidene fluoride, as well as copolymers of perflourinated monomers with partially fluorinated monomers such as copolymers of tetraflouroethylene/hexafluoropropylene/vinylidene fluoride (THV Fluorothermoplastic from Dyneon Company), polyvinylchloride, polyvinylidene chloride (PVDC, e.g., SARAN HB), ethylene vinyl alcohol (EVOH), polyolefins (e.g., polyethylene, high density polyethylene, polypropylene, and combinations thereof). Oriented and biaxially oriented polymers may be particularly preferred.

Particularly preferred barrier constructions include HDPE, PET, PETG, laminates of polyester and polyolefin (in particular PET/HDPE or HDPE/PET/HDPE), laminates of PET and EVOH, biaxially oriented nylon, PVDC, Nylon/EVOH/Nylon (OXYSHIELD OUB-R), chlorotrifluoroethylene and laminates thereof, ceramic materials including silicon oxide ($SiO_x$ where x=0.5-2 and preferably 1-2) coated thermoplastics, and ceramic coated PET (CERAMIS available from CCL Container/Tube Division, Oak Ridge, N.J.).

The thickness of the barrier layer in each of these constructions is material dependent. For single layer constructions in which HDPE is the only component, the thickness of the HDPE layer is preferably 750 micrometers or more, more preferably 1000 micrometers or more. Other constructions may be as thin as 25 micrometers or less. For example, one construction found to work well was ACLAR 11A with a thickness of 25 micrometers. A laminate of PET (37 micrometers) coated with HDPE (25 micrometers on each side) also worked well. Other potential constructions are shown in the examples.

As depicted in FIG. 1, each end of the container 20 is preferably sealed to prevent fluids within the container 20 from escaping. At end 21, the container 20 is optionally sealed by a vent assembly 30 that includes a vent plug 32 secured in the end 21 of the container 20. The vent plug 32 may be secured in the end 21 of the container 20 by any suitable technique, e.g., adhesively, by welding (chemical, spin, thermal, ultrasonic, etc.), a threaded seal with a gasket, etc.

The vent plug 32 includes a seal 34 over opening 35 in the vent plug 32. In the depicted embodiment, the opening 35 is located in the web 33 that otherwise closes the passageway through vent plug 32. In some embodiments, the opening 35 may be the same size as the web 33, but it may be preferred that the opening 35 be significantly smaller such that excessive amounts of fluids from within the container 20 cannot pass through the opening 35 after the seal 34 has been pierced or otherwise opened.

The vent assembly 30 also includes a cover 36 and associated piercing element 37. The cover 36 may serve to at least partially protect the seal 34 from unwanted opening. In addition, the cover 36 may also preferably restrain the piercing element from opening the seal 34 until opening of the seal 34 is desired. The piercing element 37 is designed to open the seal 34 by piercing, tearing, cutting, perforating, etc. For example, the piercing element may be in the form of a hollow circular die that punctures or cuts open the seal 34.

In one embodiment, cover 36 may be threadably engaged with vent plug 32 such that when cover 36 is screwed downward piercing element 37 opens seal 34. In another embodiment, cover 36 is slidably engaged with vent plug 32 such that when cover 36 is pushed downward piercing element 37 opens seal 34. Other variations will be known to those of skill in the art of, e.g., packaging.

A variety of mechanisms may be used to maintain the attached, but spaced-apart relationship between the seal 34 and the piercing element 37. For example, the cover 36 may be threadably engaged with the vent plug 32 or the container 20 itself. It may be preferred that detents or other structures be provided to prevent the cover 36 from disengaging with the vent plug 32 after the cover 36 has been partially threaded thereon. In another alternative, the threads used to assemble the cover 36 onto the vent plug 32 may be non-reversing. Any detents or other structures may also preferably restrain the cover 36 on the vent plug 32 when partially threaded thereon to prevent unwanted or accidental advancement of the cover 36 on the vent plug 32 such that the piercing element 37 does not unwantedly pierce the seal 34.

The vent assembly 30 as depicted in FIG. 1 is in a closed state in which it preferably performs the function of sealing the end 21 of the container 20 such that significant amounts of fluids within the container 20 cannot escape therefrom and, likewise, significant amounts of fluids outside of the container 20, e.g., air or other gases, cannot enter the container 20. By significant amounts, it is meant that the passage if small, infinitesimal amounts of gases and/or fluids may pass, but no functionally significant amounts which can alter the efficacy of the antiseptic prep will pass through the vent assembly 30 in its closed state. For example, typical containers packaged as to be shipped (i.e., properly filled and sealed) placed in a convection oven at 60 degrees Celsius for 14 days will typically lose 2% or less by weight of the contents, and preferably 1% or less (with a sample size of at least five containers).

FIG. 3 depicts the cover 36 after advancement onto the vent plug 32 by a sufficient distance to cause the piercing element 37 to open the seal 34. Furthermore, it may be preferred that after advancement of the cover 36 onto the vent plug 32, detents or other structures be provided to restrict or prevent reversal of the advancement of the cover 36 onto the vent plug 32. If the cover 36 is threadably engaged with the vent plug 32, rotation of the cover 36 about the axis 12 will cause the piercing element 37 to move in an arc about the axis 12 which may contribute to opening of the seal 34 as the cover 36 is rotated.

Cover 36 may be designed such that piercing element 37 comprises a vent passage or a vent passage may be provided elsewhere in cover 36. Preferably a deliberate vent passage such as a vent hole is provided to restrict the entry of air into the container so that the antiseptic composition does not flow out of the container 20 too rapidly. If the flow out of the container 20 is too rapid, it may cause unwanted dripping from the applicator. While it may be desired to limit the rate of flow out of the container 20, it is may also be desirable to provide vent holes have a sufficiently large diameter such that the antiseptic composition flows out of the container at a rate that is not too slow for use during, e.g., surgical procedures.

When balancing the desire for flow out of the container that is not too rapid or too slow, it may be preferred that the skin antiseptic composition be capable of flowing out of the container within 60 seconds or less, preferably 45 seconds or less, and possibly more preferably 30 seconds or less.

Vent holes suitable for use with applicators containing antiseptic compositions with viscosities of, e.g., 5-10 centipoise or less (e.g., aqueous compositions) that are dispensed to the interior of an open cell hydrophilic foam, may, for example, have a diameter of 2500 micrometers or less, more preferably 2000 micrometers or less, and most preferably 1800 micrometers or less. At the lower end, suitable vent holes diameters may be, e.g., 500 micrometers or more, preferably 750 micrometers or more, or possibly 1000 micrometers or more.

Until pierced or otherwise opened, the seal 34 prevents fluids from within the container 20 escaping through the opening 35. Likewise, the seal 34 preferably prevents fluids, e.g., air, sterilants (such as ethylene oxide), etc., from entering the container 20 until the seal 34 is pierced or otherwise opened. The seal 34 itself may be constructed of a variety of materials. The seal 34 may include barrier materials similar to those chosen for the container walls, although the seal 34 may also include metallic foil laminates, e.g., aluminum foil laminates. It may be preferred that the foil laminates include a thermally sealable polyolefin layer, a polyester layer, a aluminum foil layer and one or more intermediate tie layers TRISEAL TS-PE/1, available from Tekni-plex, Flemington, N.J. As an alternative to a metallic foil laminate, the seal 34 may be constructed as a laminate of two or more polymeric layers, it may be only a metallic layer, or any other suitable construction capable of providing the barrier properties described herein. In another alternative, the seal 34 may be manufactured with the same construction as the container walls as described above.

The seal 34 may be attached to the container 20 by any suitable technique, such as, adhesively, thermally (by, e.g., heat sealing, thermal welding, ultrasonically, etc.), chemical welding (using, e.g., solvents), etc.

In the depicted embodiment, the size of the opening 35 is used to restrict the passage of fluids through the vent assembly after opening of seal 34. Alternatively, the interior of the vent plug 32 could be open, i.e., not include a restricted opening 35, and the cover 36 and vent plug 32 could be designed to offer one or more restricted passageways to the passage of fluids after opening of the seal 34 (through, e.g., loose thread structures, etc.).

In another alternative for a vent assembly 30 used in connection with a skin antiseptic composition dispenser according to the present invention, it may be possible to replace a threaded vent plug 32 and cover 36 with, e.g., a bayonet-mount cover that provides for the desired function of restraining the piercing element 37 from opening the seal 34 until desired. The bayonet-mount may also provide for retention of the cover 36 on the vent plug 32 after opening of the seal 34. Other mechanisms capable of protecting the seal 34, restraining the piercing element 37, and retaining the cover 36 on the vent plug after opening of the seal 34 may be envisioned in place of the illustrative embodiments specifically described herein.

It may also be desirable to avoid "pinch points" on the dispensers of the present invention. A pinch point is a location where components in the dispenser come together in a manner that could pinch or otherwise capture a user's skin, surgical glove, clothing, etc. With respect to dispenser 10, pinch points may be avoided by providing a skirt 39 as a part of the cover 36 as seen in, e.g., FIGS. 1 and 3. The skirt 39 extends over any threads or pinch points that would otherwise be exposed before the cover 36 is advanced to open the seal 34. Although not depicted, a skirt could be provided on the dispensing assembly 40 to cover any exposed threads or pinch points.

Figure 4:
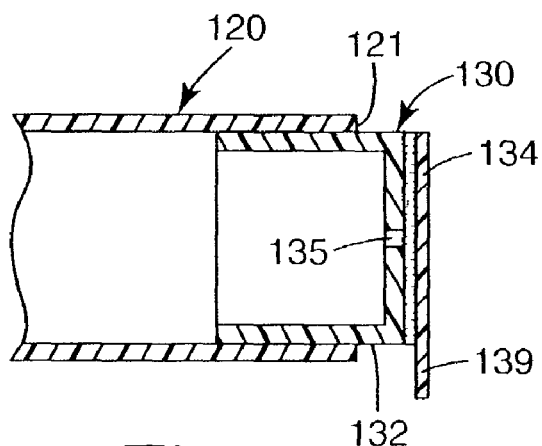
FIG. 4 is a cross-sectional view of another vent assembly for a skin antiseptic composition dispenser according to the present invention.

One example of another vent assembly 130 that does not include a piercing element is depicted in FIG. 4, where the end 121 of a container 120 is depicted along with a removable seal 134 on vent plug 132. The seal 134 covers opening 135 in the vent plug 132. The depicted seal 134 includes an optional tab 139. The tab 139 can be grasped and pulled to remove the seal 134 from vent plug 132. With the seal 134 removed, opening 135 provides a passageway into container 120 for air or other fluids. Although not depicted, vent plug 132 may include a one-way valve such that fluids can enter container 120 through opening 135 but the exit of fluids from container 120 through opening 135 is restricted.

Turning to the opposite end 22 of the container 20, one example of a dispensing assembly 40 that can be used in connection with the skin antiseptic composition dispensers of the present invention is depicted. The dispensing assembly 40 includes a barrier plug 42 located in the end 22 of the container 20. The barrier plug 42 may be secured in the end 22 of the container 20 by any suitable technique, e.g., adhesively, by welding (chemical, spin, thermal, ultrasonic, etc.), by a threaded seal with a gasket, etc.

The barrier plug 42 includes a seal 44 over an opening 45 in the barrier plug 42. Until pierced or otherwise opened, the seal 44 prevents fluids from within the container 20 escaping through the opening 45. Likewise, the seal 44 preferably prevents fluids, e.g., air, from entering the container 20 until the seal 44 is pierced or otherwise opened. The seal 44 itself may be constructed of a variety of materials. For example, the seal 44 may be formed of a laminate including a metallic foil (e.g., aluminum/polymer laminates, one of the container wall constructions, or any other suitable construction as discussed in connection with seal 34 above. The seal 44 may be attached by any suitable technique, e.g., adhesively, thermally (by, e.g., heat sealing, thermal welding, ultrasonically, etc.), chemical welding (using, e.g., solvents), etc.

The dispensing assembly 40 also includes a dispensing tip 46 and associated piercing element 47. The dispensing tip 46 may serve to at least partially protect the seal 44 from unwanted opening. In addition, the dispensing tip 46 may also preferably restrain the piercing element 47 from opening the seal 44 until opening of the seal 44 is desired. The piercing element 47 may include a barb used to open the seal 44 by piercing, tearing, cutting, perforating, etc. For example, the piercing element may be in the form of a hollow circular die that punctures or cuts open the seal 44. The dispensing tip 46 also includes openings 48 formed therein that allow the skin antiseptic composition located within container 20 to pass therethrough after the seal 44 has been opened.

A variety of mechanisms may be used to maintain the attached, but spaced-apart relationship between the seal 44 and the piercing element 47. For example, the dispensing tip 46 may be threadably engaged with the barrier plug 42 or the container 20 itself. It may be preferred that detents or other structures be provided to prevent the dispensing tip 46 from disengaging with the barrier plug 42 after the dispensing tip 46 has been partially threaded thereon. In another alternative, the threads used to assemble the dispensing tip 46 onto the barrier plug 42 may be non-reversing. Any detents or other structures may also preferably restrain the dispensing tip 46 on the barrier plug 42 when partially threaded thereon to prevent unwanted or accidental advancement of the dispensing tip 46 on the barrier plug 42 such that the piercing element 47 does not unwantedly pierce the seal 44.

The dispensing assembly 40 as depicted in FIG. 1 is in a closed state in which it preferably performs the function of sealing the end 22 of the container 20 such that significant amounts of fluids within the container 20 cannot escape therefrom and, likewise, significant amounts of fluids outside of the container 20, e.g., air or other gases, cannot enter the container 20. By significant amounts, it is meant that small amounts of gases and/or fluids may pass, but no functionally significant amounts will pass through the dispensing assembly 40 in its closed state.

After advancement of the dispensing tip 46 onto the barrier plug 42 towards end 21 of the container 20 by a sufficient distance, the piercing element 47 pierces or otherwise opens the seal 44. It may be preferred that after advancement of the dispensing tip 46 onto the barrier plug 42, detents or other structures be provided to restrict or prevent reversal of the advancement of the dispensing tip 46 onto the barrier plug 42. Because the depicted dispensing tip 46 is threadably engaged with the barrier plug 42, rotation of the dispensing tip 46 about the axis 12 causes the piercing element 47 to move in an arc about the axis 12 which may contribute to opening of the seal 44 as the dispensing tip 46 is rotated relative to the seal 44.

If both the cover 36 of the venting assembly 30 and the dispensing tip 46 of dispensing assembly 40 are threadably engaged with the skin antiseptic composition dispenser 10 at opposing ends of container 20, it may be desirable if the threads are provided such that a user can rotate the cover 36 and tip 46 in opposite directions about axis 12 to simultaneously open the seals 34 and 44 at opposing ends of the container 20.

In the depicted skin antiseptic composition dispenser 10, an applicator 50 is located over the openings 48 on dispensing tip 46. As a result, the skin antiseptic composition passes through the openings 48 and into the interior of the applicator 50 when the seal 44 is opened. The applicator 50 may be made of a variety of materials, e.g., foam, non-woven fibrous masses, woven or knitted structures, stitchbonded structures, etc.

It may be preferred that the applicator 50 be made of a material or materials that retain fluids, e.g., by absorption, adsorption, etc. One example of a potentially preferred material is an open-cell polyurethane foam.

It may, however, be preferred that the applicator 50 be constructed of a foam pad capable of passing fluids therethrough. In some instances, it may be preferred that the applicator 50 be constructed of a relatively hydrophilic foam. The hydrophilic foam may, e.g., have an apparent surface energy of 35 dynes/centimeter or more. Even higher apparent surface energy may be desirable in connection with some skin antiseptic compositions, e.g., apparent surface energy of 40 dynes/centimeter or more may be preferred. It may, however, be preferred that the hydrophilic foams used as applicators in the present invention have an apparent surface energy of 45 dynes/centimeter or more, possibly 50 dynes/centimeter or more. In some instances, it may be preferred that the hydrophilic foam be wettable by deionized water (thus having, e.g., an apparent surface energy of 70 dynes/centimeter or more). Unless otherwise indicated, apparent surface energy is determined according to the "Apparent Surface Energy Test" procedure described herein.

Surprisingly, hydrophilic foams used with aqueous skin antiseptic compositions provide superior antimicrobial efficacy as compared to traditional hydrophobic foams. Similar efficacy enhancement may be possible for aqueous enhancement may be possible for aqueous antiseptics applied using foam scrub brushes for use in, e.g., disinfecting the hands of a clinician (e.g., doctor, nurse, etc.).

It may be preferred that the minimum distances between the openings 48 in the dispensing tip 46 and the outer surface of the applicator 50 be generally consistent. Uniformity in the minimum distances between the openings 48 and the outer surface of the applicator 50 may reduce the tendency of the skin antiseptic composition to drip from the applicator 50 during dispensing of the skin antiseptic composition.

It may also be useful to control the size and distribution of the openings 48 in the dispensing tip 46 to preferably uniformly fill the applicator 50. Suitable dimensions for the openings 48 may be, e.g., 5 millimeters (mm) to 6.5 mm. The size and distribution of the openings 48 may vary based on a variety of factors, e.g., the porosity and apparent surface energy of the applicator 50 surrounding the dispensing tip 46, the viscosity and surface tension of the skin antiseptic composition within the container 20, the number of openings 48 in the tip 46, etc.

Figure 5:
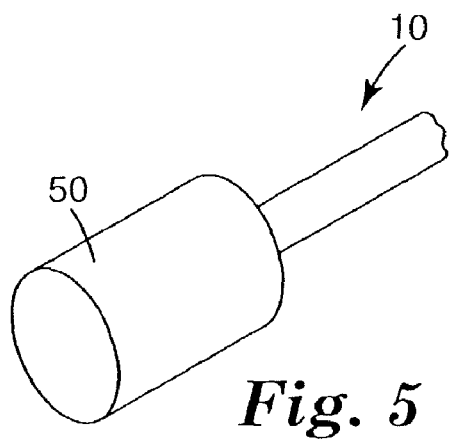
FIG. 5 is a view of another alternative pad shape for use in connection with a skin antiseptic composition dispenser according to the present invention.

The applicator 50 may take a variety of different shapes depending on the intended use of the skin antiseptic composition dispenser 10. One suitable shape for an applicator 50 may be, e.g., a circular cylindrical shape as depicted in FIG. 5. It may be preferred that cylinder be a right cylinder as depicted, although oblique cylinders may also be provided.

Figure 6:
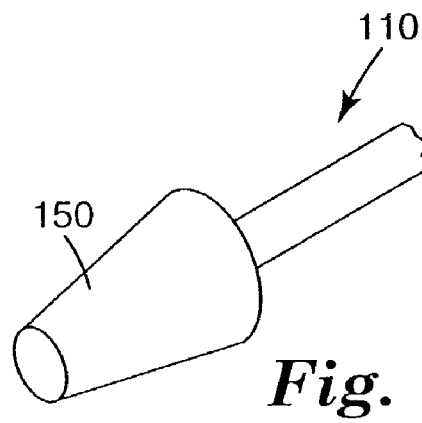
FIG. 6 is a view of another alternative pad shape for use in connection with a skin antiseptic composition dispenser according to the present invention.

Another variation on the shape of the applicators used in connection with the skin antiseptic composition dispensers of the present invention is depicted in FIG. 6. The applicator 150 depicted as a part of skin antiseptic composition dispenser 110 is in the form of a truncated cone with circular bases at each end.

Figure 7:
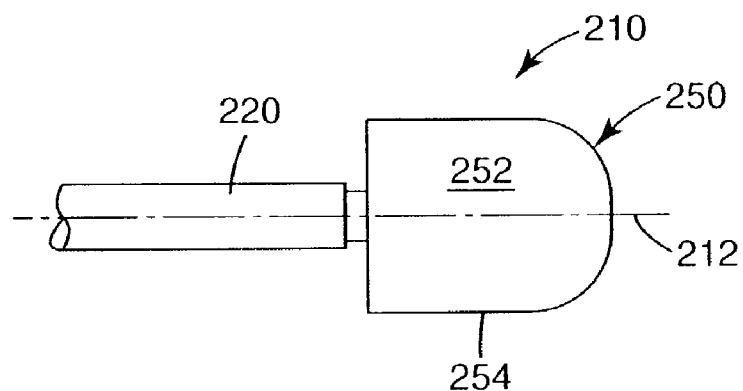
FIG. 7 is a view of another skin antiseptic composition dispenser according to the present invention.
Figure 8:
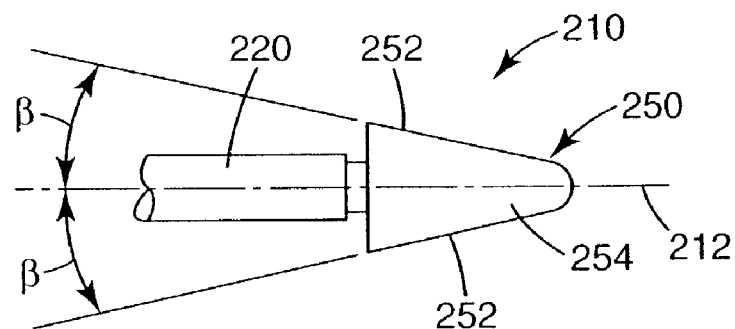
FIG. 8 is a side view of the skin antiseptic dispenser of FIG. 7.

Still another variation in the shape of an applicator used in connection with a skin antiseptic composition dispenser according to the present invention is depicted in FIGS. 7 & 8. The applicator 250 of skin antiseptic composition dispenser 210 includes two opposing major surfaces 252 separated by an edge surface 254. The edge surface 254 may be flat as shown, although other edge profiles may also be used in place of the flat profile shown.

FIG. 8 illustrates another potential feature of the applicators used in connection with skin antiseptic composition dispensers of the invention. The container 220 is elongated such that it defines a longitudinal axis 212 along its length. Although the major surfaces 252 may be located in planes that are generally parallel to the axis 212, it may be preferred that the major surfaces 252 be located in planes that are not parallel with the longitudinal axis 212 of the container 220. The major surfaces 252 of the illustrated applicator 250 are canted to form angle β (beta) with the longitudinal axis 212 in FIG. 7. The angle β (beta) may be, e.g., 2.5 degrees or more, preferably 5 degrees or more (although this is somewhat dependent on the length of the applicator 250 and the morphology of the container 220 connected thereto).

When the major surfaces of applicators are described herein as being located in a plane or defining a plane, it should be understood that the major surface need not necessarily be planar itself. Rather, the major surface may deviate somewhat from true planar surface, e.g., it may be slightly curved, undulating, or include various other deviations from a true planar surface.

A potential advantage of providing an applicator 250 with a canted major surface 252 is that during use on, e.g., the skin of a patient, the container 220 (which serves as the handle) is spaced from the patient's skin when the surface 252 is resting flat on the skin. As a result, clearance may be provided between the user's hand and the patient's skin. That clearance can reduce the likelihood of contact between the user's hand and the patient's skin, thereby improving aseptic technique in use of the skin antiseptic composition dispenser 210. If the applicator 250 is soft and/or conformable (such as a foam), the canted major surfaces 252 will not typically prevent the dispenser 210 from being used to dispense skin antiseptic composition within body orifices, e.g., vagina, rectum, etc.

Among the variations in applicators that may be described with respect to FIGS. 7 & 8, one variation in applicator design may include major surfaces that are canted at different angles from the longitudinal axis 212. In another variation, one of the major surfaces may be located in a plane that is parallel to the longitudinal axis 212, while the other major surface is canted relative to the longitudinal axis 212.

When the container 220 is in the form of an elongated tubular shape, it may be preferred that the major surfaces 252 be positioned such that the longitudinal axis 212 defined by the container 220 does not intersect one or both of the major surfaces 252.

Figure 9:
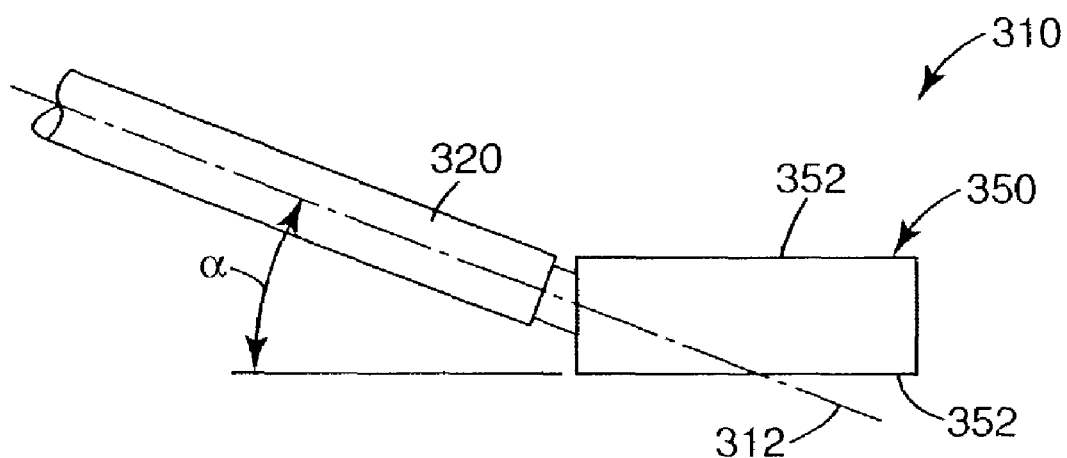
FIG. 9 is a view of another skin antiseptic composition dispenser according to the present invention.

FIG. 9 depicts another variation in applicators used in connection with the skin antiseptic composition dispensers. The applicator 350 of skin antiseptic composition dispenser 310 includes two major surfaces 352 that, in the depicted embodiment, are generally parallel with each other. The lower surface 352 is located in a plane that forms an angle α (alpha) with the longitudinal axis 312 defined by the container 320. The canted applicator 350 may be useful in providing clearance between a user's hand on the container 320 and a patient's skin during dispensing of the skin antiseptic composition within the container 320. The angle α (alpha) may preferably be 15 degrees or less, in some instances 10 degrees or less. At the opposite end of the range, it may be preferred that angle α (alpha) be 5 degrees or more.

Figure 10:
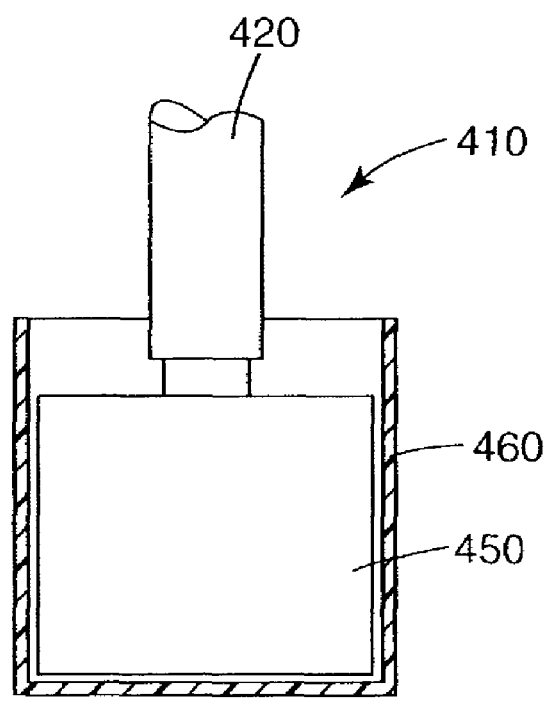
FIG. 10 is a partial cross-sectional view of an applicator of a skin antiseptic dispenser in a sleeve according to the principles of the present invention.

FIG. 10 depicts another optional feature of some embodiments of skin antiseptic composition dispensers of the present invention. The skin antiseptic composition dispenser 410 includes an applicator 450 at one end. The applicator 450 is, however, located in a sleeve 460. The sleeve 460 is preferably made of materials (e.g., films, etc.) that are impermeable to the skin antiseptic composition located within the container 420. As a result, when the skin antiseptic composition is delivered to the applicator 450 while the applicator 450 is located within sleeve 460, any of the skin antiseptic composition that escapes from the applicator 450 is retained within sleeve 460.

Furthermore, the sleeve 460 may be grasped by the user to pierce the seal(s) and dispense the antiseptic composition into the applicator. The sleeve 460 can then be removed to reveal the applicator. In this manner, the applicator is easily filled with the antiseptic composition without contamination of the applicator by the hands of the user.

The sleeve 460 is preferably retained around the applicator 450 until its removal is desired. Retention of the sleeve may be effected by a sleeve 460 that is sized to fit tightly on the applicator 450. Alternatively, the sleeve 460 may include spot welds, adhesives, or other materials/structures that assist in retaining the sleeve 460 on the applicator 450 until its removal is desired.

In one method of using a sleeve 460 in connection with a skin antiseptic composition dispenser 410, the skin antiseptic composition within container 420 is dispensed into the applicator 450 by any suitable technique (e.g., squeezing the container 420, allowing the skin antiseptic composition to drain into applicator 450 under the force of gravity, etc.). Any of the skin antiseptic composition that would otherwise drip from the applicator 450 is captured within the sleeve 460. After the skin antiseptic composition is dispensed from the container 420, the sleeve 460 and applicator 450 located therein may be compressed and released. Typically, that compression and release sequence will result in substantially all of the skin antiseptic composition returning into the applicator 450 (particularly where the applicator 450 is constructed of a hydrophilic foam). Afterwards, the sleeve 460 can be removed from the applicator 450, which is then ready for use in dispensing the skin antiseptic composition to a patient. Sleeves intended for use in the manner just described are preferably flexible to allow compression of the applicator 450 as just described.

The volume of the sleeve 460 is preferably at least as great as the volume of the skin antiseptic composition in the container 420. Typically, although not necessarily, the volume of the sleeve 460 will be at least 200% of the volume of the skin antiseptic composition in the container 420. It may be preferred that volume of the sleeve 460 be 300% or more of the volume of the skin antiseptic composition within the container 420. The volume of the sleeve is measured with an empty applicator pad fully inserted into an upright sleeve having no dispensing tip attached. The mass of water that can just fill the sleeve is recorded and converted to volume assuming a density of 1 g/cm$^3$. The volume of the sleeve should not be so great that the sleeve interferes with activating the dispenser. For example, in some embodiments the dispensing tip 46 is rotated relative to the container to open the dispensing seal 44. A sleeve that extends too far up the container would make it inconvenient to grasp the sleeve covered applicator pad in one hand and the container in the other without inadvertently grasping the sleeve.

Furthermore, it should be noted that the sleeve 460 is preferably open on the end facing the container 420 so that the sleeve 460 can retain any excess antiseptic composition and yet be easily removed. Furthermore, the opening in sleeve 460 allows a sterilant gas (e.g., ethylene oxide) to enter and sterilize the foam and be easily removed by aeration after the sterilization is complete.

The applicator 450 covered with sleeve 460 on the dispenser 410 may be further packaged in an outer package such as a bag, pouch, box, etc., that is permeable to sterilants such as ethylene oxide. In this manner, the entire exterior of the dispenser 410 can be sterilized. In use, the clinician removes the outer package and aseptically delivers the sleeve-covered applicator 450 to the sterile field. The antiseptic composition in the container 420 is released into the applicator 450 and distributed by massaging the sleeve-covered applicator 450 (if necessary). Finally, the sleeve 460 is removed and the antiseptic is applied to the patient using the applicator 450, with the container 420 acting as the handle.

In embodiments where the applicator and dispensing tip are threadably or slidably engaged with the container, the sleeve 460 is preferably sufficiently stiff to prevent getting caught in the mechanism during activation. For sleeves made of low density polyethylene, the sleeve thickness may be, e.g., greater than 50 micrometers, more preferably greater than 75 micrometers, and most preferably greater than 85 micrometers.

TEST PROTOCOLS

The following test protocols may be used to determine the physical properties discussed above with respect to the invention.

Gaseous Ethylene Oxide Permeability Test

The permeation of ethylene oxide (ETO) across various polymer films over a given unit area for a specified amount of time was measured using the following procedure. A known thickness of film was clamped between two glass test chambers (1.6 inches (4.06 cm) in diameter at the base), which were sealed to the film with an o-ring on either side. A cylinder of 100 percent ETO was placed upstream of the film under a pressure of 60 psi (0.41 MPa) and a slow, 10 ml/hr, flow of ETO was allowed to pass through the upstream chamber while the downstream chamber was swept with nitrogen gas at 40 ml/hr through a charcoal adsorption tube for 2 hours. The 8 mm×100 mm charcoal tube contained 20228 ORBO Coconut shell charcoal in two sections, front (400 mg) and back (200 mg) and is commercially available from Supelco, Bellefonte, Pa.

Ideally the ETO is trapped on the front portion. The back is analyzed to show that most if not all of the ETO is found on the front. If significant ETO (>10%) is found on the back portion it suggests that the tube was overloaded and that some ETO has passed through.

The individual sections were removed from the sampling tube and extracted for more than 2 hr with 2.0 mL acetone to desorb the ETO.

The extract solutions were analyzed by gas chromatography (GC) using the following equipment and conditions:
Instrument: Agilent Technologies 6890 GC or 5890 GC or equivalent
Column: Agilent HP-INNOWAX 30 m×0.25 mm 0.5µ film
Carrier: Helium at 1.6 mL/min
Injection: 1 µL split ½0 (200° C.)
Oven program: 30° C. (4 min hold) then at 20° C./min to 240° C. (hold 10 min)
Detection: Flame ionization (240° C.)

Under these conditions the ethylene oxide eluted as a peak at 2.0+/−0.1 minutes. A reference solution of ETO was prepared by collecting known volumes of ethylene oxide gas at room temperature and pressure. This was injected into a sealed vial containing a known volume of acetone, in which it was extremely soluble. A series of standard solutions of known concentrations was made by serial dilution of this standard with acetone.

The standards were injected under the same conditions as the sample extracts so a calibration curve of peak area vs. ETO concentration was set up. The sample concentrations were estimated by interpolation of the peak area values on this curve. Thus ETO permeation (mL/hr/in$^2$)=(ETO extract concentration×(mL gas/mL solution))×(extract solution volume (mL))/(Film area (in$^2$))×(Test time (hr))
Where: extract solution volume=2 mL
Film area=1.227 in$^2$ (7.916 cm$^2$)
Test time=2 hrs The ETO permeation was converted from mL ETO/hr/in$^2$ to mL ETO/hr/cm$^2$. Then using ETO density equal to 0.882 g/cc, ETO permeation was converted to mg ETO/hr/cm$^2$ and divided by the film thickness in micrometers to give mg of ETO/hr/cm$^2$/µm.

Gaseous Ethylene Oxide Residuals Test

Small (3 in (7.62 cm) by 5 in (12.70 cm)) dual heat sealed pouches were constructed with a seal line width of 0.48 cm from the first 12 films listed in Table 1a. The pouches were filled with 25 ml of tap water and exposed to a standard ETO sterilization cycle in 3M STERIVAC 4XL ETO Sterilizer, 3M, St. Paul, Minn. The sterilization cycle was for 4.5 hours of exposure to ETO at 37° C. with a 2.25-hour aeration time.

The contents of the pouches were removed and analyzed for ETO residual and conversion products, ethylene chlorohydrins (ECH) and ethylene glycol (EG) using ANSI/AAMI/ISO 10993-7 Biological Evaluation of Medical Devices—Part 7: Ethylene oxide sterilization and ANSI/AAMI St30: Determining Residual Ethylene Chlorohydrins and Ethylene Glycol in Medical Devices by Biotest Laboratories, Inc. Minneapolis, Minn. The results were reported in parts per million (ppm)

Apparent Surface Energy Test

The method for measuring the surface energy was AATCC Test Method 118-1983, with the modifications described below. Surface energies measured according to this modified test method are referred to herein as "apparent" surface energies. The modified AATCC test method 118-1983 determines the surface energy of a fabric or foam by evaluating the applicator's resistance to wetting by a series of selected methanol/water compositions. By employing various mixtures of methanol and water in the applicator resistance test, the measurement of a range of surface energies may be accomplished. Surface tension values were extrapolated from data given in Handbook of Chemistry and Physics 56$^{th}$ ed. page F-42, CRC Press, by plotting the data and generating a regression curve using the following formula: surface tension=−0.0000777x$^3$+0.0163756x$^2$−1.3499137x+71.1475488 where x=percent volume of methanol.

The compositions and their representative surface tensions are as follows:

| Liquid No. | Volume percent Methanol/Water | Surface Tension (dynes/cm at 20° C.) |
|---|---|---|
| 1 | 80/20 | 28 |
| 2 | 70/30 | 30 |
| 3 | 57/43 | 33 |
| 4 | 46/54 | 36 |
| 5 | 39/61 | 39 |
| 6 | 32/68 | 42 |
| 7 | 27/73 | 45 |
| 8 | 24/76 | 47 |
| 9 | 20/80 | 50 |
| 10 | 14/86 | 55 |
| 11 | 9/91 | 60 |
| 12 | 0/100 | 72 |

The test procedure was as follows. A specimen of the applicator foam material was placed such that the major surface used for testing was horizontal. For convenience the tests were conducted at 23-25° C. (room temperature) at approximately 50% relative humidity. Using the method of AATCC 118-1983 except that beginning with the lowest surface tension test liquid shown above, five drops of the test liquid were gently placed on the surface of the applicator. Note that the drop was placed on the surface, i.e. not allowed to fall onto or impact the surface. If the applicator was not homogeneous, (e.g., was a laminate or other non-homogeneous construction), the test liquid was placed in various locations on the surface that faced the impregnating antiseptic composition. If three of the five drops wicked into the applicator within 60 seconds, the test liquid of the next higher surface energy was used. When at least 3 drops remained on the applicator surface, the apparent surface energy was recorded as the value of the highest numbered liquid which had at least 3 drops absorb. (For a liquid to wet a surface the surface tension of the liquid must be less than the surface energy of the solid. More precise determination of the apparent surface energy could be accomplished by preparing fluids with surface tensions intermediate those numbered fluids shown in the table above.)

Human Skin Antimicrobial Activity

Two formulations were checked for antimicrobial activity in a method similar to ASTM Test Method E-1173-93 Standard Test for Evaluation of a Pre-operative Skin Preparation, except that the compositions were applied to the backs (considered a "dry" site) of healthy volunteers and the baseline bacterial flora counts as put forth in section 7.1 of the ASTM method were not as high. Preps were always compared to the 2-step application of BETADINE Surgical Scrub (7.5% povidone-iondine, Purdue Frederick Company, Norwalk, Conn.) and BETADINE Surgical Solution (10% povidone-iodine "paint", Purdue Frederick Company, Norwalk, Conn.) per the manufacturer's instructions. All studies were randomized block designs.

On the Study Day, two samples for baseline microbial counts were taken, one from the upper back and one from the lower back, on opposite sides of the spine. The test formulations and the control were randomized on the back-usually four across the upper back and four across the lower back. The residual bacteria were sampled from all sites 2.0 minutes after completion of application. Formulations were applied using each of two sponges, Sponge No. 3 on the applicator tip and Sponge No. 4 on its sponge stick, as described in Example 5. The prep was applied by simply painting a 2×5 inch (5.08×12.7 cm) stripe with moderate pressure in a back and forth motion for 30 seconds (approximately 30 times). BETADINE Surgical Scrub and BETADINE Surgical Solution were applied following manufacturer's directions. Briefly, BETADINE Surgical Scrub was applied with saturated gauze and scrubbed for 5 minutes, wiped off; and the BETADINE Surgical Solution applied in an outward spiral from center.

Minimums of 8 subjects were used in accordance with sections 8.2-8.3 of ASTM testing method E1173. All subjects refrained from using antimicrobial products for a minimum of 2 weeks. The average log reduction from baseline was determined for each composition. If multiple sites were run, the log reduction for each site was determined. Results were reported in average log reductions (numerical average of the log reduction values).

Note that an appropriate neutralizer was first determined for each formulation tested in accordance with ASTM testing method E1173-93 section 6.7. For most polymer systems the following neutralizing sampling solution was used: 0.4 g potassium dihydrogen phosphate, 10.1 g sodium hydrogen phosphate, 1.0 g TRITON X100 surfactant available from Union Carbide Corp., Houston Tex., 4.5 g lecithin (CAS # 8002-43-5, available from Fisher Scientific, Fairlawn, N.J. as Cat No. 03376-250), 45.0 g TWEEN 80 (ICI), 1.0 g sodium thiosulfate, and deionized water to bring the total volume to 1 liter. The sampling solution was prepared by adding all components together and heating with stirring to approximately 60° C. until dissolved. It was then placed in containers and steam sterilized.

GLOSSARY

| Acronym | Chemical Description |
|---|---|
| EVOH | Ethylene-vinyl alcohol |
| PETG | Polyethylene terephthalate glycol, modified |
| PP | Polypropylene |
| HDPE | High density polyethylene |
| PVDC | Polyvinylidene chloride |
| PET | Polyethylene terephthalate |
| EVA | Ethylene vinyl acetate |
| ETO | Ethylene oxide |
| ECH | Ethylene chlorohydrins |
| EG | Ethylene glycol |
| CXA | Co extruded Adhesive |

EXAMPLES

Example 1

Commercially available thermoplastic films of varying thickness were evaluated for ETO permeability using the Gaseous Ethylene Oxide Permeability Test described above. The descriptions of twenty-nine of the more useful films evaluated are shown in Table 1a and the thickness of the films and results of the ETO permeability test are shown in Table 1b.

A sample circle was cut from each of two bottles. One bottle was made from HDPE (commercially available as FORTIFLEX B53-35H-011 natural from Solvay Polyethylene North America, Houston, Tex.) and the other bottle was PP/EVOH/PP/PP and was used for bottling ketchup (commercially available from H. J. Heinz, Pittsburgh, Pa.). The samples were evaluated using the Gaseous Ethylene Oxide Permeability Test. The thickness of the sample and results of the ETO permeability test are shown in Table 1b.

TABLE 1a

Description of Commercially Available Films

| Film No | Product Name | Chemical Description | Source, Address |
|---|---|---|---|
| 1 | OXYSHIELD OEB | Nylon/EVOH/nylon | Allied Signal Morristown, NJ |
| 2 | OXYSHIELD OEB | Nylon/EVOH/nylon | Allied Signal Morristown, NJ |
| 3 | OXYSHIELD OEB-R | Nylon/EVOH/nylon | Allied Signal Morristown, NJ |
| 4 | OXYSHIELD OUB-R | Nylon/EVOH/nylon | Allied Signal Morristown, NJ |
| 5 | ACLAR 33C | Fluoropolymer | Allied Signal Morristown, NJ |
| 6 | ACLAR 33C | Fluoropolymer | Allied Signal Morristown, NJ |
| 7 | ACLAR 22A | Fluoropolymer | Allied Signal Morristown, NJ |
| 8 | ACLAR 22A | Fluoropolymer | Allied Signal Morristown, NJ |
| 9 | ACLAR 11A | Fluoropolymer | Allied Signal Morristown, NJ |
| 10 | ACLAR 11A | Fluoropolymer | Allied Signal Morristown, NJ |
| 11 | PACUR 6763 | PETG | Pacur Oshkosh, WI |
| 12 | PACUR 6763 | PETG | Pacur Oshkosh, WI |
| 13 | 360 HB-2 | Oriented PP | QPF Streamwood, IL |
| 14 | 250 HB-2 | Oriented PP | QPF Streamwood, IL |
| 15 | 225HBHE | Oriented PP | QPF Streamwood, IL |
| 16 | BARRIALON 26 | HDPE/PVDC/HDPE | Phoenix Films, Clearwater, FL (Distributor) Asahi Chemical Industry Co., Tokyo, Japan |
| 17 | BARRIALON 50 | PVDC | Phoenix Films, Clearwater, FL (Distributor) Asahi Chemical Industry Co., Tokyo, Japan |
| 18 | BARRIALON 56 | PP/PVDC/PP | Phoenix Films, Clearwater, FL (Distributor) Asahi Chemical Industry Co., Tokyo, Japan |
| 19 | 3M DMT Clear | PET | 3M, St. Paul, MN |
| 20 | Film Plus | HDPE/PET/HDPE | Loparex, Inc., Willowbrook, IL |
| 21 | 3M SCOTCHPAK 135 | PET/EVA | 3M, St. Paul, MN |
| 22 | CAPRAN DF | Nylon | Allied Signal Morristown, NJ |
| 23 | CAPRAN EMBLEM 2500 | Biaxial Oriented nylon | Allied Signal Morristown, NJ |
| 24 | PET-SiOx | PET/Silicon Oxide | Phoenix Films, Clearwater, FL (Distributor) Asahi Chemical Industry Co., Tokyo, Japan |
| 25 | ACLAR 22C | Fluoropolymer | Allied Signal, Morristown, NJ |
| 26 | SCOTCHPAK 29312 | PET/EVA | 3M, St. Paul, MN |
| 27 | SCOTCHPAK 6 | PET/LDPE | 3M, St. Paul, MN |
| 28 | SCOTCHPAK 33 | PET/EVA | 3M, St. Paul, MN |
| 29 | BARRIALON 25 | PVDC/HDPE | Phoenix Films, Clearwater, FL (Distributor) Asahi Chemical Industry Co., Tokyo, Japan |

TABLE 1b

Film Thickness and Results of Ethylene Oxide Permeation Test

| Film Number | Thickness mils (microns) | ml ETO/ hr/in² (ml ETO/ hr/cm²) | ETO Permeation mg ETO/ hr/cm² | mg ETO/ hr/cm²/ micron |
|---|---|---|---|---|
| 1 | 0.60 (15.24) | 0.085 (0.0132) | 11.620 | 0.762 |
| 2 | 1.00 (25.40) | 0.062 (0.0096) | 8.476 | 0.334 |
| 3 | 1.00 (25.40) | 0.013 (0.0020) | 1.777 | 0.070 |
| 4 | 1.00 (25.40) | 0.009 (0.0014) | 1.230 | 0.048 |
| 5 | 0.78 (19.81) | 0.028 (0.0043) | 3.830 | 0.193 |
| 6 | 2.00 (50.80) | 0.017 (0.0026) | 2.324 | 0.046 |
| 7 | 0.75 (19.05) | 0.012 (0.0019) | 1.640 | 0.086 |
| 8 | 3.00 (76.20) | 0.111 (0.0172) | 15.175 | 0.199 |
| 9 | 1.00 (25.40) | 0.018 (0.0028) | 2.461 | 0.097 |
| 10 | 0.60 (15.24) | 0.016 (0.0025) | 2.187 | 0.144 |
| 11 | 10.00 (254.00) | 0.015 (0.0023) | 2.051 | 0.008 |
| 12 | 5.00 (127.00) | 0.047 (0.0073) | 6.425 | 0.051 |
| 13 | 0.80 (20.32) | 0.047 (0.0073) | 6.425 | 0.316 |
| 14 | 1.22 (30.99) | 0.058 (0.0090) | 7.929 | 0.256 |
| 15 | 1.36 (34.54) | 0.022 (0.0034) | 3.008 | 0.087 |
| 16 | 2.60 (66.04) | 0.009 (0.0014) | 1.230 | 0.019 |
| 17 | 2.00 (50.80) | 0.002 (0.0003) | 0.273 | 0.005 |
| 18 | 2.40 (60.96) | 0.018 (0.0028) | 2.461 | 0.040 |
| 19 | 1.50 (38.10) | 0.001 (0.0002) | 0.137 | 0.004 |
| 20 | Total: 3.00 (76.20) By layer: 0.75/1.50/0.75 (19.05/38.10/19.05) | 0.010 (0.0016) | 1.367 | 0.018 |
| 21 | 0.86 (21.84) | 0.001 (0.0002) | 0.137 | 0.006 |
| 22 | 1.00 (25.40) | 0.001 (0.0002) | 0.137 | 0.005 |
| 23 | 0.98 (24.89) | 0.001 (0.0002) | 0.137 | 0.005 |
| 24 | 0.48 (12.19) | 0.001 (0.0002) | 0.137 | 0.011 |
| HDPE Bottle[1] Sample | 80.00 (2030) | 0.015 (0.0023) | 2.05 | 0.0032 |
| PP/ EVOH/ PP/PP Bottle[2] Sample | 60.00 (1520) | 0.077 (0.012) | 10.5 | 0.021 |

[1]HDPE bottle was blown from FORTIFLEX B53-35H-011 natural available from BP Solvay Polyethylene North America, Houston, TX. Sample was cut from the bottle.
[2]PP/EVOH/PP/PP bottle is commercially available as Heinz Ketchup from H. J. Heinz Company, Pittsburgh, PA. Sample was cut from the bottle.
In general, the data indicates that increasing the barrier film thickness decreases permeability to the sterilant gas ethylene oxide. There appeared to be differences, however, among materials of the same chemical class. For example, films 5-10 show significant permeability differences even though they belong to the same general chemical class. This may be related to the thickness of the primary barrier layer (fluorinated thermoplastic layer) and/or the crystallinity of the primary barrier layer and/or other layers in the construction. In general, film constructions 7, 11, 17, 19, and 21-24 performed the best with permeability values of less than or equal to 0.011 mg/ETO/hr/cm²/micron. It is also apparent that very thick HDPE (>2000 micron) had relatively low permeability to ethylene oxide.

Example 2

The contents of twelve pouches constructed from twelve commercially available thermoplastic films of varying thickness were analyzed for ETO, ECH, and EG using the Gaseous Ethylene Oxide Residuals Test described in Test Protocols.

The description of the films is shown in Table 1a and the thickness of the films and results of the test are shown in Table 2.

TABLE 2

Thickness of Film, Volume of Water in Pouch, and Residuals

| Film No. | Thickness mils (microns) | Volume of Water (ml) | Residuals ETO (ppm) | ECH (ppm) | EG (ppm) |
|---|---|---|---|---|---|
| 20 | 3.00 (76.20) | 45 | 20 | ND[1] | ND |
| 12 | 5.00 (127.00) | 30 | ND | ND | ND |
| 9 | 1.00 (25.40) | 57 | ND | ND | ND |
| 6 | 2.00 (50.80) | 50 | 15 | ND | ND |
| 25 | 3.00 (76.20) | 40 | 1 | ND | ND |
| 26 | 3.95 (100.33) | 40 | 34 | ND | ND |
| 27 | 2.40 (60.96) | 40 | ND | ND | ND |
| 28 | 4.00 (101.6) | 40 | ND | ND | ND |
| 16 | 2.60 (66.04) | 15 | 7 | ND | ND |
| 29 | 1.00 (25.40) | 15 | 4 | ND | ND |
| 3 | 1.00 (25.40) | 25 | 5 | ND | ND |
| 4 | 1.00 (25.40) | 25 | 9 | ND | ND |

[1]ND means not detected. The test limit of detection is 1 part per million.

Material selection was based on finding a film with very low or non-detectable levels of ETO, ECH, or EG. The Gaseous ETO Permeability Test and the Gaseous ETO Residuals Test were found to correlate very well over a range of permeabilities from 0 to 0.93 ml of ETO/hr/cm². Therefore, the simpler Gaseous ETO Residuals Test was used to qualify materials.

Example 3

Eleven coextruded trilaminated tubes (made by Teel Plastics Company, Baraboo, Wis.), which were sealed on one end, were filled with a given volume of water. The tubes had an outside diameter of 19 mm and were 16.8 cm in length. A solid plastic plug milled from HDPE was glued into the unsealed end with SCOTCH Weld DP 100 adhesive (commercially available from 3M). The filled tubes were sterilized in 3M STERIVAC 4XL 100% ETO Sterilization Cycle for 4.2 hours at 37° C. and aerated for 2.2 hours. The water was removed from the tubes and analyzed as described for Example 2. The tube chemical description, thickness, size and results of analysis of a given volume of ETO Sterilized water are reported in Table 3.

In addition, two one layer HDPE tube samples which were obtained from Norden Pac International, Kalmar, Sweden and two plastic ampoules (4 inches (10.2 cm) in length and with an inner diameter of 0.74 inches (1.88 cm) with wall thicknesses as indicated in Table 3 were milled from HDPE. The tubes and ampoules were filled with water, sterilized, and the water was analyzed in a manner similar to the trilaminate tubes.

The results are also shown in Table 3

TABLE 3

Coextruded Tube Description and Results of Analysis of ETO Sterilized Water

| Tube No. | Chemical Description | Thickness (microns) | Vol. of Water (ml) | Residuals ETO (ppm) | ECH (ppm) | EG (ppm) |
|---|---|---|---|---|---|---|
| 1 | HDPE[3]/CXA[4]/PET[1] | 533.4/50.8/76.2 | 45 | 1 | ND[5] | ND |
| 2 | HDPE/CXA/PET[1] | 482.6/50.8/127.0 | 45 | 1 | ND | ND |
| 3 | HDPE/CXA/PET[1] | 304.8/50.8/177.8 | 45 | 1 | ND | ND |
| 4 | HDPE/CXA/PET[1] | 254.0/50.8/228.6 | 45 | 1 | ND | ND |
| 5 | HDPE/CXA/PET[2] | 533.4/50.8/76.2 | 45 | 63 | 1 | 2 |
| 6 | HDPE/CXA/PET[2] | 482.6/50.8/127.0 | 45 | ND | ND | ND |
| 7 | HDPE/CXA/PET[2] | 304.8/50.8/177.8 | 45 | ND | ND | ND |
| 8 | HDPE/CXA/PET[2] | 254.0/50.8/228.6 | 45 | ND | ND | ND |
| 9 | HDPE/Admer[5]/PET[2] | 203.2/50.8/152.4 | 40 | ND | ND | ND |
| 10 | HDPE/Admer/PET[2] | 254.0/50.8/152.4 | 40 | ND | ND | ND |
| 11 | HDPE/Admer/PET[2] | 304.8/50.8/152.4 | 40 | ND | ND | ND |
| 12 | HDPE[7] | 432.0 | 40 | 301 | ND | ND |
| 13 | HDPE[7] | 432.0 | 40 | 317 | ND | ND |
| 14 | HDPE Ampoule | 2540.0 | 40 | 0.45 | ND | ND |
| 15 | HDPE Ampoule | 3175.0 | 40 | ND | ND | ND |

[1] PET is commercially available from Eastman Chemical Co., Kingsport, TN.
[2] PET is commercially available as DMT Clear Polyester from 3 M, St. Paul, MN.
[3] HDPE is commercially available as Polyethylene HHM 5202 from Phillips Marlex, Houston, TX.
[4] CXA (Co-Extruded Adhesive) is commercially available as BYNEL 2169 anhydride-modified ethylene acrylate from E. I. du Pont deNemours and Company, Wilmington, DE.
[5] Admer is commercially available as ADMER AT1614A Adhesive from Mitsui Chemicals America, Inc., Purchase, NY.
[6] ND means not detected. The test limit is 1 part per million.
[7] HDPE tubes obtained from Norden Pac International, Kalmar, Sweden.

These examples demonstrate that constructions made from PET and HDPE provide an excellent barrier to ETO. These constructions are also translucent or transparent and are relatively thin and relatively low cost to manufacture. The relatively thin polyethylene bottles (17 mil (432 microns)) had high levels (exceeding 300 ppm) of ethylene oxide. The HDPE ampoules having wall thicknesses of greater than 2500 microns, however, proved to be excellent barriers to the chemical sterilant ethylene oxide. Note that this is consistent with the results of Example 1, which showed that relatively thick HDPE was an effective barrier to ethylene oxide.

Example 4

Ceramic Barriers

Several CERAMIS tubes were obtained from CCL Container a division of CCL Ind., Don Mills, Ontario, Canada. The tubes had an internal diameter of 0.88 in (2.2 cm) and a length (measured from the base of the neck to the end of the tube) of 4.52 in (11.48 cm) and were made from a laminate constructed from the layers described in Table 4a.

TABLE 4a

Description Layers and Thickness of Laminated Tube Construction

| Layer Number | Description | Thickness (microns) |
|---|---|---|
| 1 | Co extruded polyethylene film (tube interior) | 150 |
| 2 | Lacquer laminate | 4 |
| 3 | PET SiOx (Ceramis ™) | 12 |
| 4 | Lacquer laminate | 4 |
| 5 | Co extruded polyethylene films (tube exterior) | 11 |

On one end of the tube was a neck. Two neck designs were evaluated: 1) a nasal tip with thread and 2) a larger opening with a #16 neck (threaded tip with an internal opening diameter of 0.313 in (0.795 cm) and an external thread diameter of 0.469 in (1.19 cm)). A foil laminate barrier film was thermally welded to the end of the neck of some tubes while a matching threaded cap was placed over the end of some other tubes.

Then the tubes were filled with approximately 26 ml of water through the end opposite the neck and thermally sealed using a bar heat sealer. The CERAMIS tubes were all transparent allowing visualization of the fluid level.

The tubes were sterilized in a 3M STERIVAC 4XL Ethylene Oxide sterilizer using canister 4-134 and a 37° C. cycle. The chamber of the sterilizer had a volume of 115 liters. Ethylene oxide (127 g) was delivered by the 4-134 canister yielding an ETO dose of 1104 mg/l. The tubes were removed in less than one hour after cycle completion (very little aeration time) and packed in dry ice until tested.

The tubes were tested for levels of ethylene oxide (ETO), ethylene chlorohydrins (ECH) and ethylene glycol (EG). Samples were tested according to ANSI/AAMI/ISO 10993-7 Biological Evaluation of Medical Devices—Part 7: Ethylene oxide sterilization and ANSI/AAMI ST30: Determining Residual Ethylene Chlorohydrins and Ethylene Glycol in Medical Devices by Biotest Laboratories, Inc. Minneapolis, Minn. Foil laminate tubes were also obtained from Ccl having a #16 tip and a foil seal for comparative purposes. Control tubes, which were filled with water, but not sterilized were also tested to confirm the absence of ETO, ECH and EG.

The results of the test are shown in Table 4b.

TABLE 4b

Residuals in Tubes

| Tube Description | Ethylene oxide (ppm) | Ethylene chlorohydrins (ppm) | Ethylene glycol (ppm) |
|---|---|---|---|
| Nasal Tip-No seal with cap | 10 | ND[1] | ND |
|  | 9 | ND | ND |
|  | 9 | ND | ND |
|  | 10 | ND | ND |
|  | 10 | ND | ND |
|  | 7 | ND | ND |
|  | 7 | ND | ND |
|  | 6 | ND | ND |
|  | 12 | ND | ND |
|  | 13 | ND | ND |
| Mean | 9.3 | ND | ND |
| #16 neck w/seal-no cap | 6 | <1 | <1 |
|  | 7 | <1 | <1 |
|  | 6 | <1 | <1 |
|  | 6 | <1 | <1 |
|  | 7 | <1 | <1 |
| Mean | 6.4 | <1 | <1 |
| CCL CERAMIS #16 with foil seal and cap | 4 | <1 | <1 |
|  | 3 | <1 | <1 |
|  | 3 | <1 | <1 |
|  | 4 | <1 | <1 |
|  | 4 | <1 | <1 |
|  | 4 | <1 | <1 |
| Mean | 3.6 | <1 | <1 |
| CCL Foil Tubes | 3 | <1 | <1 |
|  | 3 | <1 | <1 |
|  | 3 | <1 | <1 |
|  | 3 | <1 | <1 |
|  | 3 | <1 | <1 |
| Mean | 3 | <1 | <1 |
| Control | <1 | <1 | <1 |
|  | <1 | <1 | <1 |
|  | <1 | <1 | <1 |
| Mean | <1 | <1 | <1 |

[1]ND means not detectable. The test limit was 1 part per million.
The results indicate that the CERAMIS laminate was an excellent barrier to ethylene oxide. A combination of the foil seal and the cap over the end of the tube appeared to provide the least intrusion of ethylene oxide into the tube and a level comparable to a foil tube.

Example 5

Seven sponges, which were either commercially available or available as part of a dispenser, were evaluated for apparent surface energy using the Apparent Surface Energy Test Method described in the Test Protocols.

Table 5a contains a description of the sponges. Table 5b contains the Apparent Surface Energy of the Sponges.

TABLE 5a

Description of the Sponges

| Sponge No. | Trade Name/ Generic Name | Description | Source, Address |
|---|---|---|---|
| 1 | Illbruck Sponge | Felted version of Foam #2 compressed 2.5:1. | Illbruck Inc., Minneapolis, MN |
| 2 | Illbruck Sponge | P90Z reticulated, open pore, flexible, polyester type polyurethane sponge; pore size = 80-100 ppi; density = 1.9 lb/ft³; compressive force = 0.25 psi @ 25% compression and 0.45 psi at 65% compression. | Illbruck Inc. |
| 3 | Wilsorb polyurethane sponge | Flexible open cell, polyester, polyurethane foam; Density = 1.8 lb/ft³ (ASTM 3574) Compressive force = 0.56 psi @ 25% compression or 0.81 psi @ 65% compression; Pore size = 85 ppi | Illbruck Inc. |
| 4 | QFC-90SW Sponge Stick | Reticulated open cell polyurethane | QFC Industries, Arlington, TX |
| 5 | Allegiance-Cat. No. 4463 | Foam | Allegiance, McGaw Park, IL |
| 6 | Previal FX-Cat. No. 4vail-FX |  | Allegiance |
| 7 | Pharmaseal Scrub Care Surgical Scrub Brush sponge, Cat. No. 4454A | Reticulated open cell polyurethane sponge | Baxter Heatlhcare Corp., Pharmseal Div., Valencia, CA |

TABLE 5b

Apparent Surface Tension of Sponges

| Sponge Number | Apparent Surface Tension (dynes/cm at 23° C.) |
|---|---|
| 1 | 33 |
| 2 | 30 |
| 3 | Greater than 72 (wetted by deionized water) |
| 4 | 30 |
| 5 | 30 |
| 6 | Less than 28 (Fluid 1 did not wet) |
| 7 | 33 |

The commercially available sponges used to disinfect the skin of a patient or the hands of clinicians tested (Sponge No. 1, 2, 4, 5, 6, and 7) were found to have apparent surface energies of less than or equal to 33 dynes/cm when tested at 23° C. The hydrophilic sponge (Sponge No. 3) was found to have an apparent surface energy greater than that of water (72 dynes/cm) and much greater that 33 dynes/cm when tested at 23° C.

Example 6

The hydrophilic sponge (Sponge No. 3 in Example 5) and the hydrophobic sponge (Sponge No. 4) were used to apply antiseptic formulations A and B in Table 6a to the skin of human volunteers using the Human Skin Antimicrobial Activity described in the Test Protocols.

TABLE 6a

Antiseptic Formulations

| Component | CAS No. | Formulation A (weight percent) | Formulation B (weight percent) |
|---|---|---|---|
| Acrylate polymer[1] |  | 5.00 | 5.00 |
| Povidone-iodine |  | 7.50 | 7.50 |

TABLE 6a-continued

Antiseptic Formulations

| Component | CAS No. | Formulation A (weight percent) | Formulation B (weight percent) |
|---|---|---|---|
| USP[2] | | | |
| Lactic acid[3] | 79-33-4 | 5.00 | 5.00 |
| Malic acid[4] | 617-48-1 | 2.00 | 2.00 |
| Brij 700[5] | 9005-00-9 | 1.40 | 0.75 |
| MACKAM 50-SB[6] | 68139-30-0 | 0.00 | 1.25 |
| CRODAPHOS SG[7] | 73361-29-2 | 1.00 | 0.00 |
| AMMONYX LMDO[8] | Confidential | 0.75 | 0.00 |
| Water | | 77.35 | 78.50 |
| pH | | 3.5-4 | 3.5-4 |

[1] Amine oxide polymer (stearylmethacrylate (10%)/iotabutyl methacrylate (20%)/amine oxide of dimethylaminomethylmethacrylate (50%)/methylmethacrylate(20%)) commercially available from 3M, St. Paul, MN.
[2] Povidone-iodine USP is commercially available from BASF Corporation, Mt. Olive, NJ.
[3] Lactic acid, High Pure 88, USP is commercially available from Purac America, Lincolnshire, IL.
[4] Malic acid, DL, is commercially available from Universal Preserv-a-Chem, Edison, NJ.
[5] BRIJ 700 steareth-10 is commercially available from ICI, Wilmington, DE.
[6] MACKAM 50-SB cocamidopropylhydroxysultaine is commercially available from McIntyre Group Ltd., Unversity Park, IL.
[7] CRODAPHOS SG PPG-5-Ceteth-10 phosphate is commercially available from Croda, Inc., Parsippany, NJ.
[8] AMMONYX LMDO lauramidopropyldimethylamine oxide is commercially available from Stepan, Northfield, IL, Raw data was converted to $Log_{10}$ Colony Forming Unit (CFU)/$cm^2$. The log reduction was calculated for each of the prep formulations by subtracting the post-prepping log counts from the average of duplicate baseline log counts. Means and standard deviations of log counts and log reductions were calculated. Since the study was a randomized block design each subject received each treatment. The primary comparisons of interest were the hydrophilic Sponge No. 3 versus the hydrophobic Sponge No. 4 on a stick.

Table 6b shows the resulting log reductions.

TABLE 6b

Means and Standard Deviations of Log Reductions for Antiseptic Formulations, A and B on Sponge No. 3 and Sponge No. 4

| Prep | Sponge No. | Subjects with Base line counts equal to 2.5 or more (log reduction) | | | Subjects Base line counts less than 2.5 (log reduction) | | | All Subjects (log reduction) | | |
|---|---|---|---|---|---|---|---|---|---|---|
| | | N[1] | Mean | Std[2] | N | Mean | Std | N | Mean | Std |
| A | 4 | 4 | 0.8 | 1.8 | 4 | 1.9 | 0.5 | 8 | 1.3 | 1.4 |
| A | 3 | 4 | 2.5 | 1.1 | 4 | 2.2 | 0.2 | 8 | 2.3 | 0.7 |
| B | 4 | 4 | 0.6 | 1.4 | 4 | 1.9 | 0.9 | 8 | 1.2 | 1.3 |
| B | 3 | 4 | 2.3 | 1.2 | 4 | 2.1 | 0.2 | 8 | 2.2 | 0.8 |
| Control | Gauze | 4 | 2.5 | 1.0 | 4 | 1.7 | 1.2 | 8 | 2.1 | 1.1 |

[1] N means number of subjects
[2] Std means standard deviation.

The results surprisingly indicate that for both antiseptic formulations, A and B, hydrophilic Sponge No. 3 resulted in significantly higher log reduction compared to hydrophobic Sponge No. 4 (probability <0.03).

The preceding specific embodiments are illustrative of the practice of the invention. This invention may be suitably practiced in the absence of any element or item not specifically described in this document. The complete disclosures of all patents, patent applications, and publications are incorporated into this document by reference as if individually incorporated in total.

Various modifications and alterations of this invention will become apparent to those skilled in the art without departing from the scope of this invention, and it should be understood that this invention is not to be unduly limited to illustrative embodiments set forth herein, but is to be controlled by the limitations set forth in the claims and any equivalents to those limitations.

The invention claimed is:

1. A skin antiseptic composition dispenser comprising:
a container defining an interior volume;
skin antiseptic composition located within the interior volume of the container;
a spout attached to the container, wherein the spout comprises at least one opening therein;
a dispensing seal located between the interior volume of the container and the spout; and
a foam pad located over the spout, wherein the foam pad comprises hydrophilic foam with an apparent surface energy of 35 dynes per centimeter or more; wherein the container comprises a vent opening into the interior volume of the container, wherein the vent is located remote from the foam pad; wherein the vent comprises a vent orifice and a vent seal closing the vent orifice; and wherein the vent seal comprises a barb, wherein rotation of the vent seal and the container relative to each other advances the barb to pierce the vent seal.

2. A dispenser according to claim 1, wherein the hydrophilic foam has an apparent surface energy of 40 dynes per centimeter or more.

3. A dispenser according to claim 1, wherein the hydrophilic foam has an apparent surface energy of 45 dynes per centimeter or more.

4. A dispenser according to claim 1, wherein the skin antiseptic composition comprises an agent selected from the group consisting of iodine, an iodine complex, chlorhexidine, and combinations thereof.

5. A dispenser according to claim 1, wherein the skin antiseptic composition has a surface tension of 50 dynes per centimeter or less.

6. A dispenser according to claim 1, wherein the skin antiseptic composition has a surface tension of 45 dynes per centimeter or less.

7. A dispenser according to claim 1, wherein the skin antiseptic composition has a surface tension of 40 dynes per centimeter or less.

8. A dispenser according to claim 1, wherein the container is substantially impermeable to liquid and vapor phases of the skin antiseptic composition and wherein the container exhibits permeability to gaseous ethylene oxide of 20 mg/hr/$cm^2$ or less.

9. A dispenser according to claim 1, wherein the container comprises a tubular shape that comprises one or more flexible walls free of metallic foil layers.

10. A dispenser according to claim 9, wherein the one or more flexible walls free of metallic foil layers comprise an inner layer facing the interior volume and an outer layer facing away from the interior volume, and wherein at least one of the inner layer and the outer layer is substantially impermeable to liquid and vapor phases of the skin antiseptic composition; and further wherein at least one of the inner layer and the outer layer exhibits permeability to gaseous ethylene oxide of 20 mg/hr/$cm^2$ or less.

11. A dispenser according to claim 10, wherein the outer layer comprises polyester.

12. A dispenser according to claim 10, wherein the inner layer is selected from the group consisting of a layer of polyolefin, a layer of halogenated polyolefin, and a layer of perfluororadical-containing thermoplastic.

13. A dispenser according to claim 1, wherein the container comprises an elongated tubular shape defining a longitudinal axis, and wherein the foam pad comprises at least one major surface, and wherein the at least one major surface is located in a plane that is not parallel to the longitudinal axis, and further wherein the longitudinal axis does not intersect the at least one major surface.

14. A dispenser according to claim 1, wherein the container comprises an elongated tubular shape defining a longitudinal axis, and wherein the foam pad comprises two opposing major surfaces, and wherein each major surface defines a plane that is not parallel to the longitudinal axis, and further wherein the longitudinal axis does not intersect at least one of the two opposing major surfaces.

15. A dispenser according to claim 14, wherein the longitudinal axis does not intersect either of the two opposing major surfaces.

16. A dispenser according to claim 1, wherein the dispensing seal comprises a seal layer attached over a dispensing orifice in the container.

17. A dispenser according to claim 1, further comprising a liquid impermeable sleeve sized to contain the foam pad, wherein the foam pad is located within the sleeve.

18. A dispenser according to claim 17, wherein the sleeve comprises a sleeve volume of 200% or more of a volume of the skin antiseptic composition in the container.

* * * * *

UNITED STATES PATENT AND TRADEMARK OFFICE
CERTIFICATE OF CORRECTION

PATENT NO. : 7,261,701 B2
APPLICATION NO. : 10/263518
DATED : August 28, 2007
INVENTOR(S) : Robert A. Davis It is certified that error appears in the above-identified patent and that said Letters Patent is hereby corrected as shown below:

Page 2, Column 2 (Other Publications)
Line 2, delete "Retrived" and insert -- Retrieved --, therefor.

Column 5
Line 16 (Approx.), delete "DRAWING' and insert -- DRAWINGS --, therefor.

Column 6
Line 38, delete "moncaprate," and insert -- monocaprate, --, therefor.
Line 44, delete "octenidene," and insert -- octenidine, --, therefor.

Column 8
Line 36 (Approx.), delete "scalable" and insert -- sealable --, therefor.

Column 9
Line 8, delete "terephalate)," and insert -- terephthalate), --, therefor.
Line 10-11, delete "chlorotriflouroethylene" and insert -- chlorotrifluoroethylene --, therefor.
Line 12, delete "perflourinated" and insert -- perfluorinated --, therefor.
Line 13-14, delete "tetraflouroethylene" and insert -- tetrafluoroethylene --, therefor.

Column 17
Line 52, after "ppm" insert -- . --.

Column 18
Line 54 (Approx.), delete "povidone-iondine," and insert -- povidone-iodine, --, therefor.

Column 20
Line 53, delete "PET-SiOx" and insert -- PET-SiO$_x$ --, therefor.

Column 22
Line 67, after "3" insert -- . --.

Column 23
Line 2 (below Table 3), delete "3 M," and insert -- 3M, --, therefor.

Column 24
Line 62, delete "Ccl" and insert -- CCL --, therefor.

UNITED STATES PATENT AND TRADEMARK OFFICE
CERTIFICATE OF CORRECTION

PATENT NO. : 7,261,701 B2
APPLICATION NO. : 10/263518
DATED : August 28, 2007
INVENTOR(S) : Robert A. Davis It is certified that error appears in the above-identified patent and that said Letters Patent is hereby corrected as shown below:

Column 26
Line 22, delete "Heatlhcare" and insert -- Healthcare --, therefor.
Line 23, delete "Pharmseal" and insert -- Pharmaseal --, therefor.

Column 27
Line 18 (Approx.), delete "(10%)/iotabutyl" and insert -- (10%)/isobutyl --, therefor.
Line 27 (Approx.), delete "Unversity" and insert -- University --, therefor.
Line 30, delete "IL," and insert -- IL. --, therefor.
Line 59 (Approx. below Table 6b), after "subjects" insert -- . --.

Column 28
Line 35, delete "wberein" and insert -- wherein --, therefor.

Column 12
Line 24, after "aluminum/polymerlaminates" insert -- ) --.

Signed and Sealed this

Sixth Day of May, 2008

JON W. DUDAS
*Director of the United States Patent and Trademark Office*